(12) United States Patent
Schinski et al.

(10) Patent No.: US 11,306,041 B2
(45) Date of Patent: Apr. 19, 2022

(54) CATALYTIC SYNTHESIS OF SUPER LINEAR ALKENYL ARENES USING RHODIUM CATALYSTS

(71) Applicant: University of Virginia Patent Foundation, Charlottesville, VA (US)

(72) Inventors: William Schinski, San Rafael, CA (US); Alan Goldman, Highland Park, NJ (US); Thomas B. Gunnoe, Palmyra, VA (US); Michael S. Webster-Gardiner, Mims, FL (US); Nichole Schwartz, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 67 days.

(21) Appl. No.: 16/499,756

(22) PCT Filed: Mar. 30, 2018

(86) PCT No.: PCT/US2018/025501
§ 371 (c)(1),
(2) Date: Sep. 30, 2019

(87) PCT Pub. No.: WO2018/183916
PCT Pub. Date: Oct. 4, 2018

(65) Prior Publication Data
US 2021/0163377 A1    Jun. 3, 2021

Related U.S. Application Data

(60) Provisional application No. 62/478,853, filed on Mar. 30, 2017.

(51) Int. Cl.
*C07C 2/66* (2006.01)
*B01J 21/04* (2006.01)
(Continued)

(52) U.S. Cl.
CPC ............ *C07C 2/66* (2013.01); *B01J 21/04* (2013.01); *B01J 21/08* (2013.01); *B01J 23/42* (2013.01);
(Continued)

(58) Field of Classification Search
CPC .... C07C 2/66; C07C 5/03; C07C 2/84; C07C 15/58; C07C 67/343; C07C 15/46;
(Continued)

(56) References Cited

U.S. PATENT DOCUMENTS 4,962,253 A    10/1990  Dubois
6,127,590 A *  10/2000  Taube ............... C07B 37/00
                                                585/435

(Continued)

FOREIGN PATENT DOCUMENTS

WO    2016154416 A1    9/2016

OTHER PUBLICATIONS

International Search Report dated Jul. 10, 2018.
(Continued)

*Primary Examiner* — Sharon Pregler
(74) *Attorney, Agent, or Firm* — Thomas|Horstemeyer, LLP

(57) ABSTRACT

Catalytic methods for synthesis of super linear alkenyl arenes and alkyl arenes are provided. The methods are capable of synthesizing super linear alkyl and alkenyl arenes from simple arene and olefin starting materials and with high selectivity for linear coupling. Methods are also provided for making a 2,6-dimethylnapthalene (DMN) or 2,6-methylethylnapthalene (MEN).

21 Claims, 6 Drawing Sheets

(51) Int. Cl.
*B01J 21/08* (2006.01)
*B01J 23/42* (2006.01)
*B01J 23/46* (2006.01)
*B01J 29/44* (2006.01)
*B01J 31/18* (2006.01)
*B01J 31/22* (2006.01)
*C07C 5/333* (2006.01)
*C07C 5/41* (2006.01)

(52) U.S. Cl.
CPC ............. *B01J 23/464* (2013.01); *B01J 29/44* (2013.01); *B01J 31/183* (2013.01); *B01J 31/2226* (2013.01); *B01J 31/2291* (2013.01); *C07C 5/333* (2013.01); *C07C 5/41* (2013.01); *B01J 2231/32* (2013.01); *B01J 2531/0244* (2013.01); *B01J 2531/822* (2013.01); *B01J 2531/827* (2013.01); *C07C 2521/04* (2013.01); *C07C 2521/08* (2013.01); *C07C 2523/46* (2013.01); *C07C 2529/44* (2013.01); *C07C 2531/22* (2013.01)

(58) Field of Classification Search
CPC ..... C07C 15/073; C07C 15/40; C07C 17/266; C07C 2531/22; C07C 2/76; C07C 15/44; C07C 22/08; C07C 69/618; C07C 69/65; C07C 69/734; B01J 31/00; B01J 31/1815; B01J 31/189; B01J 31/2226; B01J 31/2291

See application file for complete search history.

(56) References Cited

U.S. PATENT DOCUMENTS 9,302,954 B2\* 4/2016 Goldman .................. C07C 5/52
2001/0037044 A1 11/2001 Matsumoto et al.
2018/0065116 A1\* 3/2018 Gunnoe .................. C07C 2/66

OTHER PUBLICATIONS

Hollas et al. "Synthesis and Characterization of Pd Complexes of a Carbazolyl/Bis(lmine) NNN Pincer Ligand" Inorganic Chemistry. (Mar. 2011) vol. 50, p. 3674, Chart 1.

\* cited by examiner

CATALYTIC SYNTHESIS OF SUPER LINEAR ALKENYL ARENES USING RHODIUM CATALYSTS

CROSS-REFERENCE TO RELATED APPLICATIONS

This application is the 35 U.S.C. § 371 national stage application of PCT Application No. PCT/US2018/025501, filed Mar. 30, 2018, which claims priority to, and the benefit of, U.S. provisional application entitled "CATALYTIC SYNTHESIS OF 'SUPER' LINEAR ALKENYL ARENES USING AN EASILY PREPARED RH(I) CATALYST" having Ser. No. 62/478,853 filed Mar. 30, 2017.

STATEMENT REGARDING FEDERALLY SPONSORED RESEARCH OR DEVELOPMENT

This invention was made with government support under Grant No. DE-SC0000776, awarded by the Department of Energy. The government has certain rights in the invention.

TECHNICAL FIELD

The present disclosure generally relates to organic synthesis.

BACKGROUND

Alkyl arenes are used in a wide range of products including plastics, detergents, fuels, fine chemicals and as a liquid scintillator. Since the development of a commercially viable route to produce alkyl benzene sulfonates on a large scale in the 1940s, they have formed the basis of the detergent industry (Kocal, J. A.; Vora, B. V.; Imai, T. *Appl. Catal. A* 2001, 221, 295; Olah, G. A.; Molnár, Á. *Hydrocarbon chemistry*; Wiley & Sons: New York, 1995; Tadros, T. In Kirk-Othmer Encyclopedia of Chemical Technology; John Wiley & Sons, Inc.: 2000) Initial synthetic routes to make alkyl benzenes produced highly branched alkyl groups and, thus, the products were called branched alkyl benzenes, (BAB). The highly branched alkyl chain of BAB rendered them resistant to biodegradation and resulted in pollution of lakes and streams (Kosswig, K. In *Ullmann's Encyclopedia of Industrial Chemistry*; Wiley-VCH Verlag GmbH & Co. KGaA: 2000; de Almeida, J. L. G.; Dufaux, M.; Taarit, Y. B.; Naccache, C. *J. Am. Oil. Chem. Soc.* 1994, 71, 675) Linear alkyl benzenes (LAB), which, in contrast to their moniker, are primarily composed 2- and 3-phenyl alkanes (Olah 1995) are more readily biodegraded than BAB and constitute the majority of alkyl benzene sulfonates produced today (Kosswig 2000). Currently, LAB are produced from benzene and α-olefins using acid-based catalysts, typically either a solid acid catalyst, HF or $AlCl_3$ in combination with a Brønsted acid (Kocal 2001; Röper 2000; Perego, C.; Ingallina, P. *Green Chem.* 2004, 6, 274). These acid-based catalytic processes generate carbocationic intermediates and, as a result, are not able to produce truly linear 1-phenylalkanes, which we label as "super" linear alkyl benzenes (SLAB) to differentiate them from LAB that do not contain 1-phenylalkanes. Even utilizing shape- and size-selective zeolite catalysts, to our knowledge, the generation of SLAB is not possible (Cao, Y.; Kessas, R.; Naccache, C.; Ben Taarit, Y. *Appl. Catal. A* 1999, 184, 231)

There is a long felt need in the art for compositions and methods useful for better catalysis and catalytic conversion of simple arenes and α-olefins. There remains a need for catalysts, compositions, and methods that overcome the aforementioned deficiencies.

SUMMARY

Catalysts, catalytic methods, and compositions are provided that overcome one or more of the aforementioned deficiencies. In one or more aspects, methods are provided for making alkenyl arenes starting from arenes and alpha olefins. The methods include contacting an arene and an olefin in the presence of an effective amount of a rhodium catalyst and an oxidant at an elevated temperature for a period of time to produce the alkenyl arenes.

The methods can be performed with a wide variety of rhodium catalysts. The catalysts can include Rh ligand complexes. In some aspects, the catalysts include heterogeneous Rh catalyst such as Rh on metal oxide. In some aspects, the rhodium catalyst has a structure according to the following formula

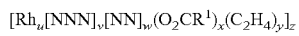

where [NNN] is a tridentate nitrogen donor ligand, [NN] is a bidentate nitrogen donor ligand, and $R^1$ is a substituted or unsubstituted $C_1$-$C_{12}$ alkyl or heteroalkyl; where u, v, w, x, y, and z are integers such that u is 1 or 2; v and w are 0 or 1 so long as v+w is less than or equal to 1; x is an integer from 0 to 4; y is an integer from 0 to 2; and z is 1 or 2. In some aspects, v+w is 1; and z is 1. In some aspects, v is 1; and x+y is 1. In some aspects, w is 1; and x+y is 2. In some aspects, $R^1$ is $CH_3$ or $CF_3$.

In some aspects, the ligands include pincer ligands. For example, the [NNN] can be an NNN pincer ligand having a structure according to the formula

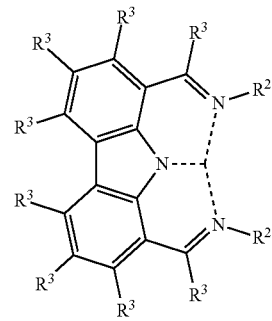

where each occurrence of $R^2$ is independently a hydrogen or a substituted or unsubstituted $C_1$-$C_3$ alkyl or heteroalkyl; and wherein each occurrence of $R^3$ is independently a hydrogen, a halogen, a hydroxyl, or a substituted or unsubstituted $C_1$-$C_3$ alkyl or heteroalkyl.

In some aspects, [[NN] is a bidentate nitrogen donor ligand having a structure according to either of the following formulas

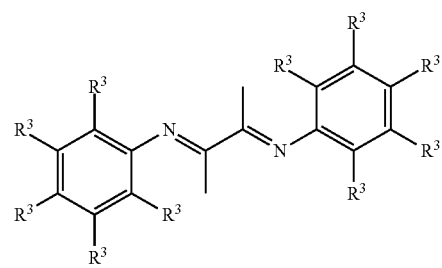

-continued

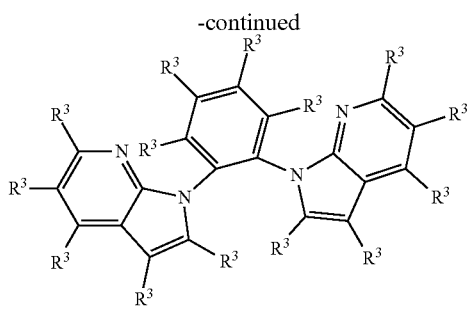

where each occurrence of $R^3$ is independently a hydrogen, a halogen, a hydroxyl, or a substituted or unsubstituted $C_1$-$C_3$ alkyl or heteroalkyl.

The methods can also be used to make linear alkyl arenes. For example, the method can further include dehydrogenation of the alkenyl arenes to form alkyl arenes. In some aspects, the dehydrogenation includes contacting the alkenyl arenes and hydrogen in the presence of a hydrogenation catalyst at a second elevated temperature for a second period of time to produce the alkyl arenes. The second elevated temperature can be about 100° C. to about 300° C. In some aspects, the dehydrogenation includes combining the alkenyl arenes and the ethanol at an elevated pressure of about 100 psig to about 5000 psig. The second period of time is about 1 hour to about 72 hours. In some aspects, a linear to branched ratio (L:B ratio) of the alkyl arenes is about 2:1 to about 99:1.

In some aspects, methods are provided for making a 2,6-dimethylnapthalene (DMN) or 2,6-methylethyl-napthalene (MEN). The methods can include making a pentenyl or hexenyl toluene by a method described herein, followed by dehydroaromatization of the pentenyl or hexenyl toluene to form the DMN or MEN. The dehydroaromatization can include contacting the pentenyl or hexenyl toluene with a combination of a dehydrogenation catalyst and a zeolite catalyst. In some aspects, the dehydrogenation catalyst is an iridium complex with a pincer-type ligand.

In some aspects, the arene is a mono-substituted benzene; and the alkenyl arenes produced include one or both of a meta-substituted alkenyl arene and a para-substituted alkenyl arene. The methods can favor the production of meta- and para-substituted alkenyl arenes over ortho-substituted alkenyl arenes. For example, in some aspects a total amount of the meta-substituted alkenyl arene and the para-substituted alkenyl arene is about 85 mol % to about 100 mol % based upon a total amount of the alkenyl arene.

The methods can be used with a wide variety of arene starting materials. The arene can be a mono-substituted benzene, a di-substituted benzene, or a tri-substituted benzene. The arene can include simple mono-substituted benzenes such as toluene, chlorobenzene, and anisole. The arenes can also include polyaromatic compounds such as substituted and unsubstituted naphthalene, anthracene, tetracene, and other polyaromatic compounds having any number of fused aromatic and heteroaromatic rings. In some aspects, the polyaromatic has from 2 to 5 fused aromatic and heteroaromatic rings.

The catalysts and methods provided herein present an alternative to the acid-based catalytic synthesis of alkyl arenes. In some aspects, utilization of a transition metal-mediated catalytic reaction that operates via C—H activation of the arene and olefin insertion into metal-aryl bonds results in a linear to branched (L:B) ratio of alkyl (or unsaturated) arene product depends on the regioselectivity of olefin insertion (i.e., 2,1-versus 1,2-insertion) and, potentially, the relative rates.

In some aspects, the catalysts and methods provide a lower cost and more efficient process for the synthesis of dimethylnaphthalene (DMN) based on the use of linear toluene alkylation combined with higher selectivity dehydroaromatization. This process has lower feedstock costs than the Amoco/British Petroleum, xylene-based route; and higher DMN selectivity in the dehydroaromatization step than shown for the Chevron, toluene-based route.

In some aspects, the Rh catalyzed conversions of arenes and olefins to vinyl or alkenyl arenes can be accomplished with a Rh catalyst that is non-halogenated and non-ligated or non-halogenated/ligated Rh catalyst precursors (i.e., no Rh—X bonds where X=F, Cl, Br, I), which provides advantages for non-corrosive conditions.

Also, in some aspects in situ oxidants can be used (e.g., Cu(II) salts) that can be recycled using purified oxygen or air. In some aspects, air can be used as an oxidant without any other oxidants present. In some aspects, reactions provided herein with mono-substituted terminal olefins (so called α-olefins) give high selectivity for products that give 1-substituted aryl alkanes when hydrogenated (so called "super linear alkenyl or alkyl arenes"). Also, in some aspects the reaction products from reactions with mono-substituted arenes are selective for meta and para (1,3- and 1,4-disubstituted) products. This contrasts with the selectivity of current commercial processes for alkyl arene synthesis (e.g., Friedel-Crafts or zeolite catalysts).

Other systems, methods, features, and advantages of catalysts, catalytic methods, and compositions will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 1A is a graph of the total turnover of alkenyl products as a function of time in hours at 120° C., 150° C., and 180° C. FIG. 1B is a graph of the linear to branched ratio (L:B ratio) as a function of time in hours at 150° C. and 180° C.

FIG. 2A is a graph of the total turnover of alkenyl products as a function of time in hours for CuX$_2$ equals Cu(OAc)$_2$ and Cu(OPiv)$_2$. FIG. 2B is a graph of the linear to branched ratio (L:B ratio) as a function of time in hours for CuX$_2$ equals Cu(OAc)$_2$ and Cu(OPiv)$_2$.

FIG. 4A is a graph of the total turnover of alkenyl products as a function of time in hours for 0.01 mol %, 0.005 mol %, and 0.001 mol % catalyst. FIG. 4B is a graph of the linear to branched ratio (L:B ratio) as a function of time in hours for 0.01 mol %, 0.005 mol %, and 0.001 mol % catalyst.

DETAILED DESCRIPTION

Figure 1A:
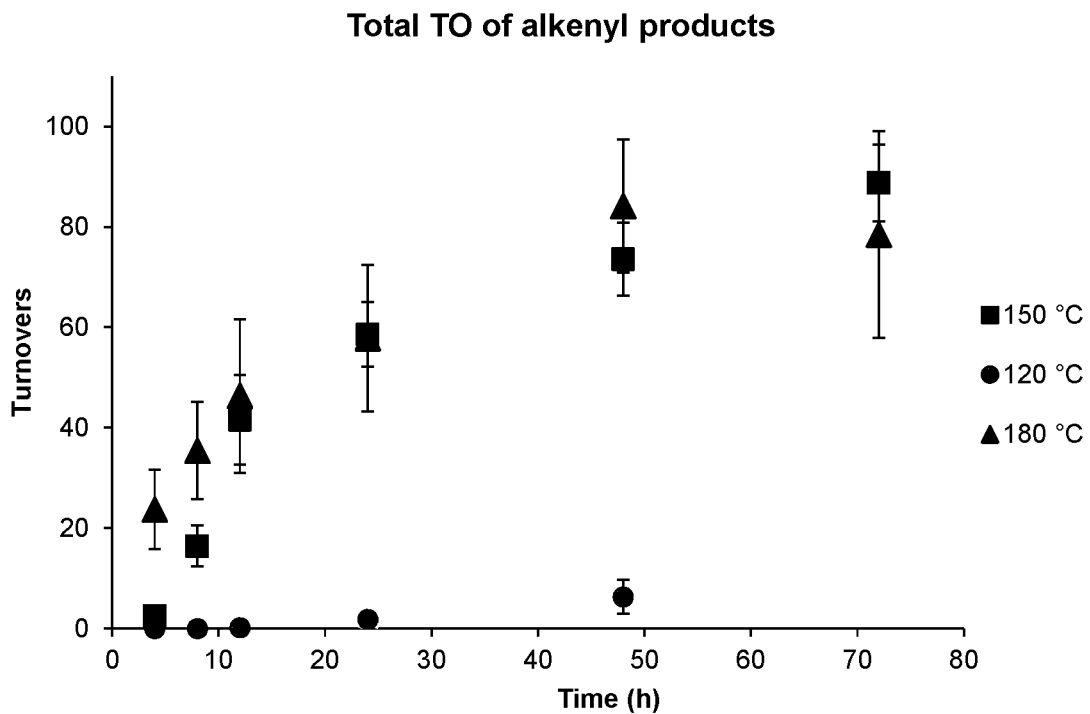
FIGS. 1A-1B show the effect of temperature on catalytic conversion of benzene and propylene using [Rh(µ-OAc)(η²-$C_2H_4$)$_2$]$_2$ as a catalyst. Reaction conditions: 0.001 mol % catalyst (relative to benzene), 240 equivalents Cu(OAc)2, 25 psig propylene. L:B for 120° C. excluded analysis due to lack of TO. Error bars represent standard deviations of at least three independent experiments.

Currently, linear alkyl benzenes (LAB's) are produced from benzene and α-olefins using acid-based catalysts, typically either a solid acid catalyst, HF or AlCl$_3$ in combination with a Brønsted acid (Scheme 1). These acid-based catalytic processes generate carbocationic intermediates and, as a result, are not able to produce truly linear 1-phenylalkanes, which we refer to herein as "super linear alkyl benzenes" (SLAB) to differentiate them from LAB that do not contain 1-phenylalkanes. In exemplary aspects, monosubstituted benzenes using the methods provided herein can, when reacted with alpha olefins, produce para substituted super linear alkenyl benzenes as depicted in Scheme 2.

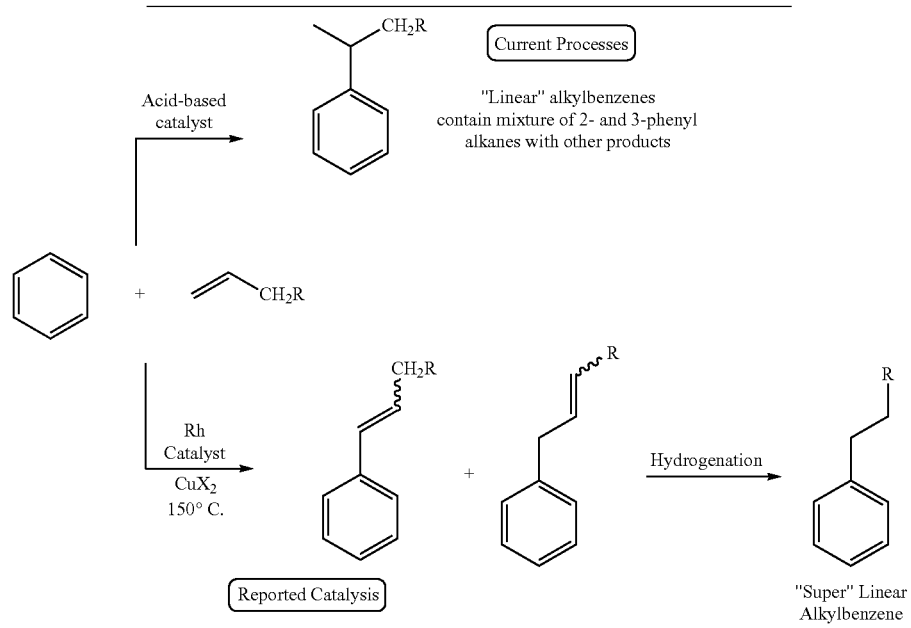

Scheme 1. Current route for the synthesis of linear alkyl benzenes (top path) and an exemplary route for the synthesis of super linear straight-chain vinyl/allyl and alkyl benzenes (bottom path).

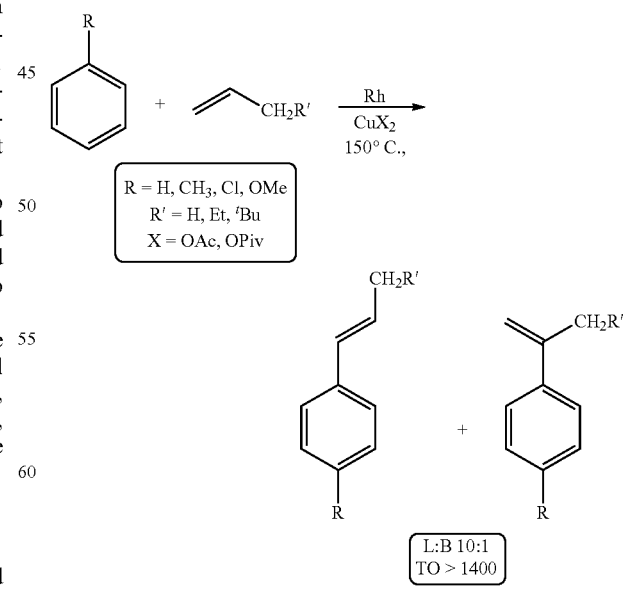

Scheme 2. Exemplary synthetic route for the production of para-substituted super linear alkenyl benzenes with high selectivity.

In exemplary aspects, methods provided herein can be used to synthesize 2,6-Dimethylnaphthalene (2,6-DMN or DMN) from toluene and 1-pentene. 2,6-DMN is a starting material used in a number of industries, most importantly for high-performance polyester fibers and films. For example, polyethylene naphthalate (PEN) can be prepared from the oxidation of 2,6-DMN. An exemplary method for synthesis of PEN starting from toluene and 1-pentene is depicted in Scheme 3. The process includes a coupling reaction of 1-pentene with toluene to give mixed isomers of straight-chain n-pentenyl toluenes that are converted in a following step via dehydroaromatization to mixed dimethyl naphthalenes. The coupling reaction can be conducted with a metal catalyst, especially a Rh based catalyst described herein. Both homogeneous and heterogeneous catalysts have been demonstrated in toluene alkenylation/alkylation process. The dehydroaromatization reaction can use a combination of a dehydrogenation catalyst and a zeolite catalyst. An example of the dehydrogenation catalyst is an iridium complex with a pincer-type ligand. By the substitution of 1-hexene in place of 1-pentene in the toluene alkylation step, one can also synthesize 2-ethyl-6-methyl-naphthalene, also referred to as methylethylnaphthalene (MEN).

Scheme 3. Exemplary process for preparation of dimethylnaphthalene from toluene and 1-pentene.

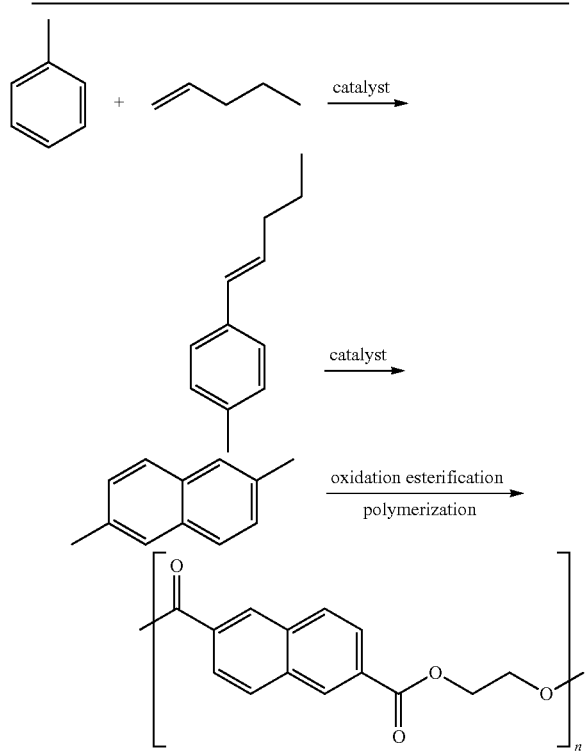

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The term "about," as used herein, means approximately, in the region of, roughly, or around. When the term "about" is used with a numerical value, it modifies that value by extending the boundaries above and below the numerical value set forth. For example, in some aspects, the term "about" is used herein to modify a numerical value above and below the stated value by a variance of ±20%, ±15%, or ±10% of the stated value. In some aspects, the term "about" can reflect traditional uncertainties in experimental measurements and/or traditional rounding according to significant figures of the numerical value.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In some aspects, a straight chain or branched chain alkyl has 30 or fewer carbon atoms in its backbone (e.g., $C_1$-$C_{30}$ for straight chains, $C_3$-$C_{30}$ for branched chains), 20 or fewer, 12 or fewer, or 7 or fewer. Likewise, in some embodiments cycloalkyls have from 3-10 carbon atoms in their ring structure, e.g. have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, or from one to six carbon atoms in its backbone structure. Likewise, "lower alkenyl" and "lower alkynyl" have similar chain lengths. Throughout the application, preferred alkyl groups are lower alkyls. In some embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In some embodiments, the "alkylthio" moiety is represented by one of —S-alkyl, —S-alkenyl, and —S-alkynyl. Representative alkylthio groups include methylthio, and ethylthio. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, and tert-butoxy. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula:

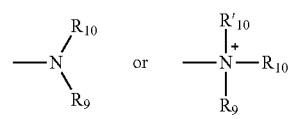

wherein $R_9$, $R_{10}$, and $R'_{10}$ each independently represent a hydrogen, an alkyl, an alkenyl, —$(CH_2)_m$—$R_8$ or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In some embodiments, only one of $R_9$ or $R_{10}$ can be a carbonyl, e.g., $R_9$, $R_{10}$ and the nitrogen together do not form an imide. In still other embodiments, the term "amine" does not encompass amides, e.g., wherein one of $R_9$ and $R_{10}$ represents a carbonyl. In additional embodiments, $R_9$ and $R_{10}$ (and optionally $R'_{10}$) each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

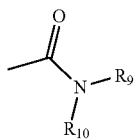

wherein $R_9$ and $R_{10}$ are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, and 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl", as used herein, refers to an alkyl group substituted with an aryl group (e.g., an aromatic or heteroaromatic group).

The term "carbocycle", as used herein, refers to an aromatic or non-aromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, and —CN.

The term "carbonyl" is art-recognized and includes such moieties as can be represented by the general formula:

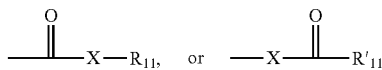

wherein X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "heteroatom" as used herein means an atom of any element other than carbon or hydrogen. Examples of heteroatoms are boron, nitrogen, oxygen, phosphorus, sulfur and selenium. Other heteroatoms include silicon and arsenic.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, $-ON$, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

As used herein, an "analog", or "analogue" of a chemical compound is a compound that, by way of example, resembles another in structure but is not necessarily an isomer (e.g., 5-fluorouracil is an analog of thymine).

As used herein, a "derivative" of a compound refers to a chemical compound that may be produced from another compound of similar structure in one or more steps, as in replacement of H by an alkyl, acyl, or amino group or a substituent described above.

Rhodium Catalysts

Applicants have found that various rhodium catalysts can be used to catalyze the coupling of olefins and arenes to form super linear vinyl or alkenyl arenes. In some aspects, the rhodium catalysts include a Rh catalyst that is non-halogenated and/or non-ligated or non-halogenated/ligated Rh catalyst precursors (e.g. no Rh—X bonds where X=F, Cl, Br, I), which provides advantages for non-corrosive conditions.

In some aspects, the rhodium catalyst is a rhodium ligand complex having a structure according to the formula

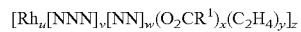

where [NNN] is a tridentate nitrogen donor ligand, [NN] is a bidentate nitrogen donor ligand, and $R^1$ is a substituted or unsubstituted $C_1$-$C_{12}$ alkyl or heteroalkyl. In the above formula, u, v, w, x, y, and z are integers such that u is 1 or 2; v and w are 0 or 1 so long as v+w is less than or equal to 1; x is an integer from 0 to 4; y is an integer from 0 to 2; and z is 1 or 2. In some aspects, when v+w is 1, then z is also 1. In some aspects, when v is 1 then x+y is 1. In some aspects, when w is 1 then x+y is 2. In some aspects of catalysts according to the above formula, u is 2, v and w are both 0, x+y is 4, and z is 1.

In the formula for rhodium catalysts described above, [NNN] is a tridentate nitrogen donor ligand. A variety of tridentate nitrogen donor ligands are known in the art. For example, the tridentate nitrogen donor ligand can be an NNN pincer ligand. In some aspects, [NNN] can have a structure according to the formula

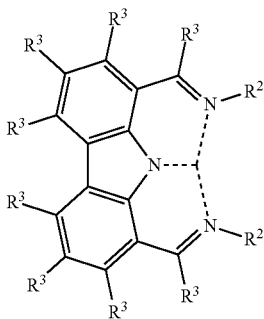

where each occurrence of $R^2$ is independently a hydrogen or a substituted or unsubstituted $C_1$-$C_3$ alkyl or heteroalkyl; and each occurrence of $R^3$ is independently a hydrogen, a halogen, a hydroxyl, or a substituted or unsubstituted alkyl or heteroalkyl having from 1 to 12, 1 to 6, or 1 to 3 carbon atoms.

In the formula for rhodium catalysts described above, [NN] is a bidentate nitrogen donor ligand. A variety of bidentate nitrogen donor ligands are known in the art. For example, the bidentate nitrogen donor ligand can have a structure according to any one of the following formulas

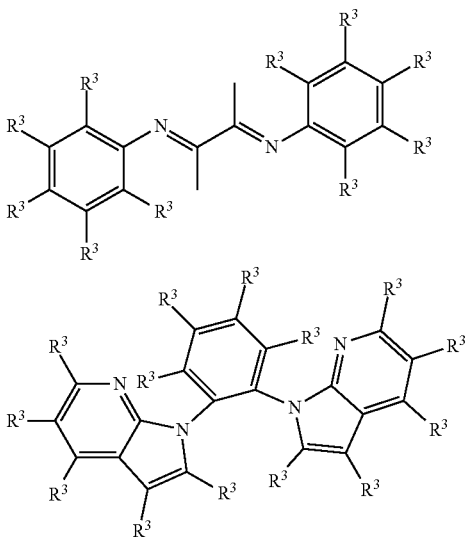

where each occurrence of $R^3$ is independently a hydrogen, a halogen, a hydroxyl, or a substituted or unsubstituted alkyl or heteroalkyl having from 1 to 12, 1 to 6, or 1 to 3 carbon atoms. In some aspects, $R^3$ is H or F.

In the above formulas, $R^1$ is a substituted or unsubstituted $C_1$-$C_{12}$ alkyl or heteroalkyl, a substituted or unsubstituted $C_1$-$C_6$ alkyl or heteroalkyl, or a substituted or unsubstituted $C_1$-$C_3$ alkyl or heteroalkyl. In some aspects, $R^1$ is $CH_3$ or $CF_3$.

In some aspects, the rhodium catalyst is a supported rhodium catalyst. A supported rhodium catalyst can include a catalyst according to the above formula where v is 1 and [NNN] is a tridentate nitrogen donor ligand having a linker group covalently attached thereto. In some aspects, a supported rhodium catalyst can include a catalyst according to the above formula where w is 1 and [NN] is a bidentate nitrogen donor ligand having a linker group covalently attached thereto. The linker group can include a substituted or unsubstituted alkyl or heteroalkyl group. The linker group can tether the rhodium catalyst to a substrate such as a zeolite substrate, a metal substrate, a silicon substrate, or any other suitable substrate material.

In some aspects, the rhodium catalyst includes a Rh(I) catalyst. However, in some aspects, the rhodium catalyst includes one or both of a Rh(II) catalyst and a Rh(III) catalyst. The rhodium catalyst can include rhodium nanoparticles or microparticles. The rhodium catalyst can also include heterogeneous Rh(II) and/or Rh(III) catalysts such as Rh on $SiO_2$, Rh on $Al_2O_3$, or Rh on a zeolite such as ZSM-5. In some aspects, the rhodium catalyst includes $Rh_2(OAc)_4$.

Other features and advantages of the rhodium catalysts will be or become apparent to one with skill in the art upon examination of the examples. It is intended that all such additional features and advantages be included within this description, be within the scope of the present disclosure, and be protected by the accompanying claims.

Catalytic Synthesis of Super Linear Alkenyl Arenes

Methods are provided for the catalytic synthesis of super linear alkenyl arenes from arene and alpha olefin precursors. The methods can include using any one or more of the rhodium catalysts described herein. The catalytic methods can convert simple arenes from petrochemical feedstocks (e.g., benzene or toluene) and simple α-olefins (e.g., propylene, 1-hexene and longer chain α-olefins) to straight-chain alkyl or vinyl/allyl arenes with high selectivity for linear isomers.

The methods can include contacting an arene and an olefin in the presence of an effective amount of a rhodium catalyst and an oxidant at an elevated temperature for a period of time to produce the alkenyl arenes. The contacting can be accomplished by any suitable methods known in the art including mixing, combining, or stirring the reactants with the catalyst or in contact with the catalyst, flowing the reactants over, past, or through a supported catalyst, or a combination thereof.

The reactions can in some aspects be carried out at relatively mild conditions. The reactions can be effective even at very low catalyst loading levels. In some aspects, the a loading of the rhodium catalyst is about 0.001 mol % to about 0.1 mol %, about 0.001 mol % to about 0.05 mol %, or about 0.001 mol % to about 0.01 mol % relative to the arene. The reactions can also function with relatively mild oxidants such as a Cu(II) salt or even air in some instances. The oxidant can be present at an amount from about 50 equivalents to about 5,000 equivalents, about 100 equivalents to about 2,500 equivalent, or about 500 equivalents to about 1,000 equivalents relative to the loading of the rhodium catalyst. The reactions can be carried out at elevated temperature ranging from about 100° C. to about 250° C., about 130° C. to about 200° C., or 150° C. to about 180° C.

The reactions can also be carried out for a period of time ranging from hours to days, e.g. from about 12 hours to about 120 hours. The methods are also highly selective and can be performed with high turnover number. For example, in some aspects the alkenyl arenes are produced with a turnover number of about 50 to about 500, about 70 to about 250, or about 70 to about 100. The reactions are selective for linear alkenyl arenes. In some aspects, a linear to branched ratio (L:B ratio) of the alkenyl arenes is about 2:1 to about 99:1, about 25:1 to about 99:1, about 50:1 to about 99:1, about 75:1 to about 99:1, or about 90:1 to about 100%.

The methods are also selective for meta- and para-substitution as compared to the ortho-substitution favored by prior methods. The methods can include converting a mono-substituted phenyl and an olefin to metal-substituted alkenyl arenes and/or to para-substituted alkenyl arenes. In some aspects, a total amount of the meta-substituted alkenyl arene and the para-substituted alkenyl arene is about 85 mol % to about 100 mol %, about 90 mol % to about 100 mol %, or about 95 mol % to about 100 mol % based upon a total amount of the alkenyl arene. Suitable mono-substituted phenyls can include toluene, chlorobenzene, and anisole. The reactions can proceed with simple olefins such as propylene, 1-pentene, neohexene, and isobutylene. In some aspects, the olefin is a linear or branched, substituted or unsubstituted alpha olefin having from 2 to about 15, 3 to about 15, 3 to about 12, or 3 to about 7 carbon atoms. In some aspects, the arene is benzene and the olefin is ethylene so that the alkenyl arene produced is styrene. In some aspects, the styrene is produced with over 95% yield and a ratio of styrene to trans-stilbene of at least 98:1.

In some aspects, an acid is added to to improve one or both of a longevity of the rhodium catalyst and a linear to branched ratio (L:B ratio) of the alkenyl arenes.

In some aspects, the methods can include making a 2,6-dimethylnapthalene (DMN) or 2,6-methylethyl-napthalene (MEN). The methods can include making a pentenyl or hexenyl toluene using a coupling method described herein, followed by dehydroaromatization of the pentenyl or hexenyl toluene to form the DMN or MEN. The dehydroaromatization can include contacting the pentenyl or hexenyl toluene with a combination of a dehydrogenation catalyst and a zeolite catalyst. Suitable dehydrogenation catalysts can include an iridium complex with a pincer-type ligand.

Other features and advantages of the methods will be or become apparent to one with skill in the art upon examination of the examples. It is intended that all such additional features and advantages be included within this description, be within the scope of the present disclosure, and be protected by the accompanying claims.

Hydrogenation of Super Linear Alkenyl Arenes to Form Super Linear Alkyl Arenes

Upon dehydrogenation, the alkenyl arenes can yield alkyl arenes, e.g. because of the selectivity of the coupling the dehydrogenation can yield super linear alkyl arenes with high selectivity. For example, a linear to branched ratio (L:B ratio) of the alkyl arenes can be about 2:1 to about 99:1, about 25:1 to about 99:1, about 50:1 to about 99:1, or about 90:1 to about 100 percent.

The hydrogenation can be accomplished via any of a number of hydrogenation catalysts, e.g. by contacting the alkenyl arenes and hydrogen in the presence of a hydrogenation catalyst at a second elevated temperature for a second period of time to produce the alkyl arenes. The second elevated temperature can be about 100° C. to about 300° C.

A number of hydrogenation catalysts are available to catalyze the hydrogenation of alkenes. In some aspects, the hydrogenation catalyst is Pd on carbon, Pt on carbon, Pt on alumina, or Ni on silica. For example, the catalyst can include about 5% Pd or Pt on carbon, which has proven to be an affective catalyst.

In some aspects, the method includes comprises combining the alkenyl arenes with ethanol and the hydrogenation catalyst under a hydrogen atmosphere at an elevated pressure. The elevated pressure can be about 100 psig to about 250 psig of hydrogen.

The reaction can proceed relatively quickly, producing high turnover and selectivity within about 12 hours to about 24 hours.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Experimental Section
General Considerations.

All manipulations were performed under an atmosphere of dry nitrogen using standard Schlenk or high vacuum techniques and/or in a glovebox. Glovebox purity was maintained by periodic nitrogen purges and was monitored by an oxygen analyzer ($O_2$<15 ppm for all reactions). Dry, oxygen-free solvents were employed throughout and stored over molecular sieves. Benzene was dried by passage through columns of activated alumina. Pentane was dried over sodium benzophenone ketyl. GC/MS was performed using a Shimadzu GCMS-QP2010 Plus system with a 30 m×0.25 mm SHRXI-5MS column with 0.25 μm film thickness using electron impact (EI) ionization. GC/FID was performed using a Shimadzu GC-2014 system with a 30 m×90.25 mm HP5 column with 0.25 μm film thickness.

Phenyl acetate, 3-pentylbenzene, 2-pentylbenzene, n-pentylbenzene, cumene, n-propylbenzene, α-methylstyrene, trans-β-methylstyrene, and biphenyl production was quantified using linear regression analysis of gas chromatograms of standard samples of authentic product. A plot of peak area ratios versus molar ratios gave a regression line. For the GC/FID instrument, the slope and correlation coefficient of the regression lines were 2.51 and 0.97 (phenyl acetate), 1.78 and 0.98 (3-pentylbenzene), 1.82 and 0.98 (2-pentylbenzene), 2.09 and 0.98 (n-pentylbenzene), 0.68 and 0.99 (cumene), 0.73 and 0.99 (n-propylbenzene), 0.74 and 0.99 (α-methylstyrene), 0.72 and 0.99 (trans-β-methylstyrene), 1.55 and 0.98 (biphenyl), 2.78 and 0.99 (1-pentene), 2.9 and 0.99 (2-pentene), respectively. Quantification of allyl benzene was estimated using the slope and correlation coefficient of the regression lines for cumene. Quantification of cis-β-methylstyrene was estimated using the slope and correlation coefficient of the regression lines for trans-β-methylstyrene. For the GC/MS instrument, the slope and correlation coefficient of the regression lines were 0.63 and 0.99 (4-ethylanisole), 0.56 and 0.99 (4-ethylchlorobenzene), 0.29 and 0.99 (3-ethylchlorobenzene), 0.55 and 0.99 (n-propylbenzene), and 0.55 and 0.99 (n-pentylbenzene). Quantification of 2-propylanisole, 3-propylanisole, 4-propylanisole, and 4-isopropylanisole was estimated using the slope and correlation coefficient of the regression lines for 4-ethylanisole.

Quantification of 2-propylchlorobenzene, 3-propylchlorobenzene, 4-propylchlorobenzene, 3-isopropylchlorobenzene, and 4-isopropylchlorobenzene was estimated using the slope and correlation coefficient of the regression lines for 3-ethylchlorobenzene and 4-ethylchlorobenzene. Quantification of 2-propyltoluene, 3-propyltoluene, 4-propyltoluene, 3-isopropyltoluene, 4-isopropyltoluene, and isobutyl benzene was estimated using the slope and correlation coefficient of the regression lines for cumene. Quantification of 3,3-dimethylbutylbenzene was estimated using the slope and correlation coefficient of the regression lines for n-pentylbenzene. Identification of peaks due to linear versus branched products was determined by studying the mass fragmentation patterns. Branched products have substantially larger peak 15 m/z units less than the molecular ion peak relative to linear products. Linear products reveal loss of alkyl chain up to the allylic position.

Propylene and isobutylene were purchased in gas cylinders from GTS-Welco and used as received. All other reagents were purchased from commercial sources and used as received. $[Rh(\eta^2-C_2H_4)_2(\mu-OAc)]_2$ (1) was prepared according to literature procedures (Werner, H.; Poelsma, S.; Schneider, M. E.; Windmüller, B.; Barth, D. *Chem. Ber.* 1996, 129, 647).

Catalytic Oxidative Hydrophenylation of Propylene.

A representative catalytic reaction is described. A stock solution containing 1 (0.005 g, 0.012 mmol, 0.001 mol % of rhodium), hexamethylbenzene (0.075 g, 0.45 mmol), and benzene (200 mL) was prepared in a volumetric flask. Glass Fisher-Porter reactors were charged with stock solution (10 mL) and $Cu(OAc)_2$ (0.050 g, 0.28 mmol). The vessels were sealed, pressurized with propylene (25 psig), and subsequently stirred and heated to 150° C. The reaction was sampled every 4 h for the first 12 h, then at the 24 h time point, and then every 24 h subsequently. At each time point, the reactors were cooled to room temperature, sampled, recharged with propylene, and reheated. Aliquots of the reaction (<200 µL) mixture were analyzed by GC/FID using relative peak areas versus the internal standard (hexamethylbenzene).

Hydrogenation General Procedure.

To a glass Fischer-Porter reactor, an aliquot of reaction sample was mixed in a 1:1 V:V mix with absolute ethanol, approximately 50 mg of 5% Pt on carbon and a stir bar were added. The reactor was then pressured with hydrogen and released (3×70 psi) before being placed under 150 psig of hydrogen while stirring for 17 hours. The reaction was then degassed, and the mixture was analyzed by GC/MS or GC/FID.

Olefin Identity Experiments.

A stock solution containing 1 (0.01 mol % relative to benzene), hexamethylbenzene (20 equiv. relative to 1), and benzene (200 mL) was prepared in a volumetric flask. When using liquid olefins, 2000 equivalents (relative to 1) of olefin were added to the stock solution. Glass Fisher-Porter reactors were charged with stock solution (10 mL) and oxidant (240 equiv. relative to 1). The vessels were sealed, charged with olefin if necessary (25 psig), and subsequently stirred and heated to 150° C. The reaction was sampled after 24 h, 48 h, and 72 h. At each time point, the reactors were cooled to room temperature, sampled, recharged with propylene, and reheated. Aliquots of the reaction (<200 µL) mixture were analyzed by GC/MS using relative peak areas versus the internal standard (hexamethylbenzene). Using neo-hexane 30(8) TO of 100% linear product (3,3-dimethylbutyl)benzene and 27(6) TO of the olefin coupled product 2,2,4,6,6-pentamethylheptane was observed after 72 hours.

Oxidant Loading Experiments.

A stock solution containing 1 (0.001 mol % relative to benzene), hexamethylbenzene (20 equiv. relative to Rh), and benzene (200 mL) was prepared in a volumetric flask. Glass Fisher-Porter reactors were charged with stock solution (10 mL) and $Cu(OAc)_2$ (60, 120 or 240 equiv. relative to 1). The vessels were sealed, charged with propylene (25 psig), and subsequently stirred and heated to 150° C. The reaction was sampled every 4 h for the first 12 h, then at the 24 h time point, and then every 24 h subsequently. At each time point, the reactors were cooled to room temperature, sampled, recharged with propylene, and reheated. Aliquots of the reaction (<100 µL) mixture were analyzed by GC/FID using relative peak areas versus the internal standard (hexamethylbenzene).

Temperature Variation Experiments.

A stock solution containing 1 (0.001 mol % relative to benzene), hexamethylbenzene (20 equiv. relative to Rh), and benzene (200 mL) was prepared in a volumetric flask. Glass Fisher-Porter reactors were charged with stock solution (10 mL) and $Cu(OAc)_2$ (240 equiv. relative to 1). The vessels were sealed, charged with propylene (25 psig), and subsequently stirred and heated to 120, 150 or 180° C. The reaction was sampled every 4 h for the first 12 h, then at the 24 h time point, and then every 24 h after that. At each time point, the reactors were cooled to room temperature, sampled, recharged with propylene, and reheated. Aliquots of the reaction (<100 µL) mixture were analyzed by GC/FID using relative peak areas versus an internal standard (hexamethyl benzene).

Rhodium Loading Experiments.

Three stock solutions containing 1 (0.001 mol % relative to benzene, 0.005 mol % relative to benzene, or 0.01 mol % relative to benzene), hexamethylbenzene (20 equiv. relative to Rh), and benzene (200 mL) was prepared in volumetric flasks. Glass Fisher-Porter reactors were charged with stock solution (10 mL) and $Cu(OAc)_2$ (240 equiv. relative to 1). The vessels were sealed, charged with propylene (25 psig), and subsequently stirred and heated to 150° C. The reaction was sampled every 4 h for the first 12 h, then at the 24 h time point, and then every 24 h subsequently. At each time point, the reactors were cooled to room temperature, sampled, recharged with propylene, and reheated. Aliquots of the reaction (<100 µL) mixture were analyzed by GC/FID using relative peak areas versus an internal standard (hexamethylbenzene).

High Turnover Experiment.

A stock solution containing 1 (0.001 mol % relative to benzene), hexamethylbenzene (20 equiv. relative to 1), and benzene (200 mL) was prepared in a volumetric flask. Glass Fisher-Porter reactors were charged with stock solution (10 mL) and $Cu(OPiv)_2$ (2400 equiv. relative to 1). The vessels were sealed, charged with propylene (50 psig), and subsequently stirred and heated to 150° C. The reaction was sampled at 12 h, 24 h, 48 h, 72 h and 96 h. At each time point, the reactors were cooled to room temperature, sampled, recharged with propylene, and reheated. Aliquots of the reaction (<200 µL) mixture were analyzed by GC/FID using relative peak areas versus the internal standard (hexamethylbenzene). After the 48 hour sampling an additional 1200 equiv. $Cu(OPiv)_2$ was added.

Olefin Identity Experiments.

A stock solution containing 1 (0.01 mol % relative to benzene), hexamethylbenzene (20 equiv. relative to 1), and benzene (200 mL) was prepared in a volumetric flask. When using liquid olefins, 2000 equivalents (relative to 1) of olefin were added to the stock solution. Glass Fisher-Porter reactors were charged with stock solution (10 mL) and oxidant (240 equiv. relative to 1). The vessels were sealed, charged with olefin if necessary (25 psig), and subsequently stirred and heated to 150° C. The reaction was sampled after 24 h, 48 h, and 72 h. At each time point, the reactors were cooled to room temperature, sampled, recharged with propylene, and reheated. Aliquots of the reaction (<200 μL) mixture were analyzed by GC/MS using relative peak areas versus the internal standard (hexamethylbenzene). Using neohexene 30(8) TO of 100% linear product (3,3-dimethylbutyl) benzene and 27(6) TO of the olefin coupled product 2,2,4,6,6-pentamethylheptane was observed after 72 hours.

Arene Identity Experiments.

A stock solution containing 1 (0.01 mol % relative to arene), hexamethylbenzene (20 equiv. relative to Rh), and arene (100 mL) was prepared in a volumetric flask. Glass Fisher-Porter reactors were charged with stock solution (10 mL) and oxidant (240 equiv relative to 1). The vessels were sealed, charged with propylene (25 psig), and subsequently stirred and heated to 150° C. The reaction was sampled after 24 h, 48 h, and 72 h. At each time point, the reactors were cooled to room temperature, sampled, recharged with propylene, and reheated. Aliquots of the reaction (<100 μL) mixture were analyzed by GC/MS using relative peak areas versus the internal standard (hexamethylbenzene).

Isomerization of 1-Pentene.

A stock solution containing 1 (0.01 mol % relative to benzene), hexamethylbenzene (20 equiv. relative to 1), and benzene (200 mL) was prepared in a volumetric flask. Either 1-pentene or 2-pentene (2000 equiv. relative to 1) was added to the stock solution. Glass Fisher-Porter reactors were charged with stock solution (10 mL) and, if required, $Cu(OAc)_2$ (240 equiv. relative to 1) was added. An initial sample (100 μL) was taken before heating (t=0 h) and analyzed by GC/FID to determine the ratio of 1-pentene and 2-pentene. The vessels were sealed, stirred and heated to 150° C. The reaction was sampled at 48 h and 72 h. At each time point, the reactors were cooled to room temperature, sampled at 0° C. and reheated. Aliquots of the reaction (<100 μL) mixture were analyzed by GC/FID using relative peak areas versus the internal standard (hexamethylbenzene). The total concentration of pentenes decreases over time due to the high volatility.

Results and Discussion

Figure 1B:
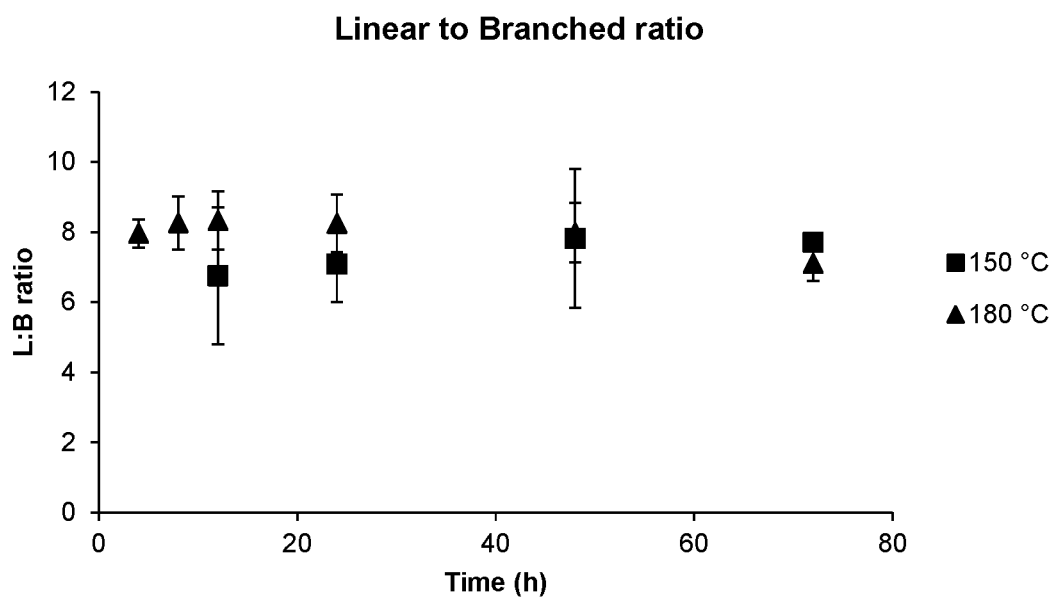

Heating a 10 mL benzene solution of complex 1 (0.001 mol % relative to benzene) to 150° C. under 25 psi of propylene with $Cu(OAc)_2$ (240 equiv. relative to 1) over 48 hours affords functionalized benzene products with a linear:branched (L:B) ratio of 8:1 (Scheme 4 and FIGS. 1A-1B). Unless stated otherwise, complex 1 mol % is given relative to benzene and Cu(II) equivalents are relative to 1. The L:B ratio for the products is determined based on straight-chain products that would result from Pt s (i.e., allylbenzene, cis-β-methylstyrene and trans-β-methylstyrene) compared to branched product from hydrogenations (i.e., α-methylstyrene). The turnovers (TO) of alkenyl benzenes at 48 hours were 73(7). Since two equivalents of Cu(II) are used per equivalent of vinyl or allyl arene product the maximum yield is 50% of the amount of Cu(II). Thus, 73(7) turnovers using 240 equiv. of $Cu(OAc)_2$ corresponds to ~60% yield. Aliquots of the reaction mixture were analyzed by GC/FID using relative peak areas versus an internal standard (hexamethylbenzene). Detection limits for the instruments were equivalent to ~1 TO of product.

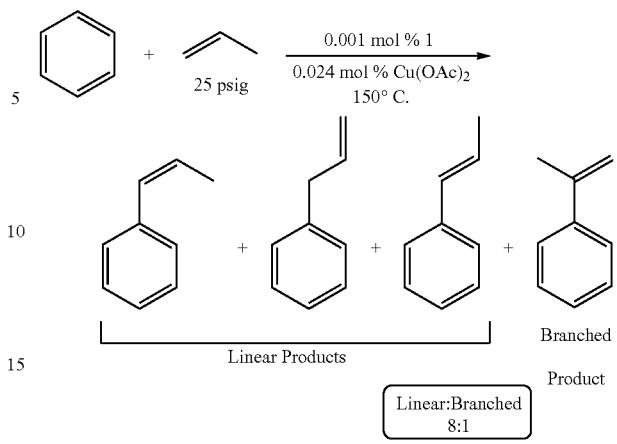

Scheme 4. Oxidative coupling of benzene and propylene to cis-β-methylstyrene, allylbenzene, trans-β-methystryene and α-methylstyrene. A linear:branched ratio of 8:1 was observed.

For the reaction of benzene and propylene catalyzed by 1, four products were observed (TO after 48 h are given for each): allylbenzene: 31(2), cis-β-methylstyrene: 5(1), trans-β-methystryene: 28(4), and α-methylstyrene: 9(1). The 1.1:1 ratio of allylbenzene to β-methystryene could suggest that there is negligible difference between β-hydride elimination from the terminal $CH_3$ group or the benzylic position of the putative {Rh—C($CH_3$)$HCH_2$Ph} intermediate. In contrast to Pt(II) catalysts for olefin hydroarylation, these Rh catalyzed reactions do not give difunctionalized products (McKeown, B. A.; Foley, N. A.; Lee, J. P.; Gunnoe, T. B. *Organometallics* 2008, 27, 4031).

Figure 2A:
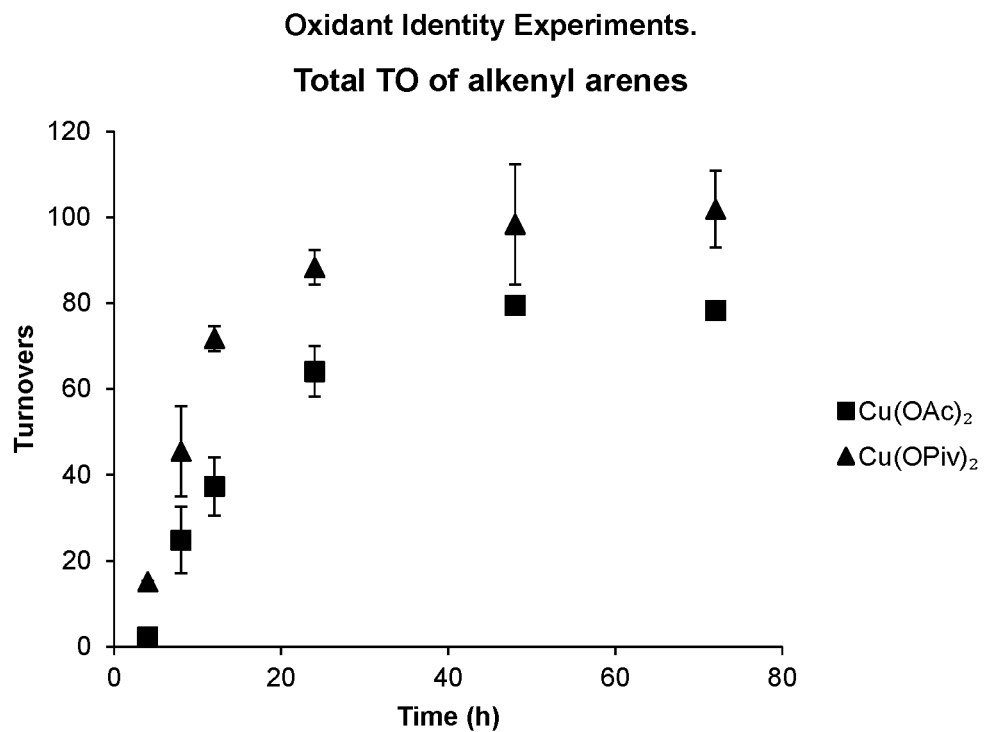
FIGS. 2A-2B show the effect of the oxidant (CuX$_2$) identity on conversion of benzene and propylene [Rh(µ-OAc)(η²-$C_2H_4$)$_2$]Z as a catalyst. Reaction conditions: 0.01 mol % catalyst, 240 equiv. CuX$_2$, 25 psig propylene. Error bars represent standard deviations of at least three independent experiments.
Figure 2B:
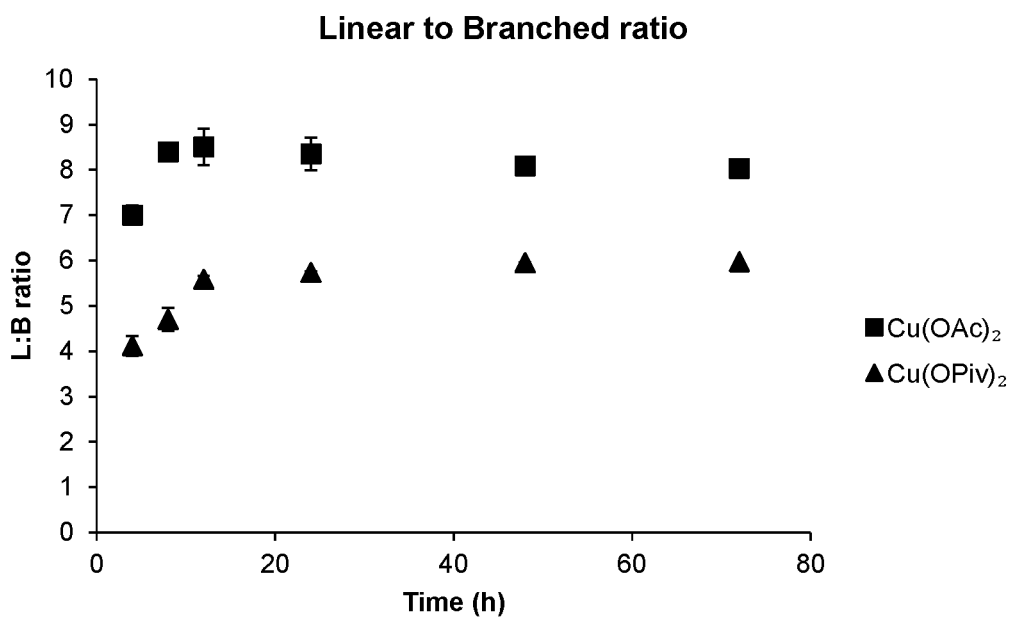
Figure 3:
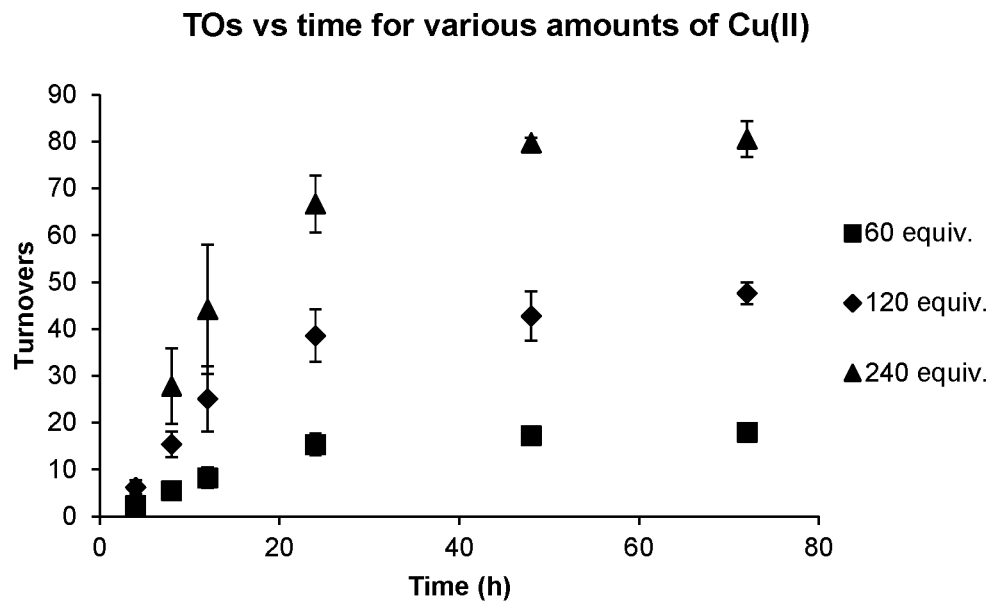
FIG. 3 shows the effect of oxidant concentration on conversion of benzene and propylene using [Rh(µ-OAc)(η²-$C_2H_4$)$_2$]$_2$ as a catalyst. Reaction conditions: 0.01 mol % catalyst (relative to benzene), 60, 120, or 240 equivalents Cu(OAc)$_2$, 150° C., 25 psig propylene. Error bars represent standard deviations of at least three independent experiments.

Using $CuCl_2$ or CuO at 150° C. or 180° C. over 48 hours afforded minimal vinyl or allyl benzene products. In contrast, use of 240 equiv. of $Cu(OPiv)_2$ (Piv=pivalate) gave 72(3) TO after 12 hours with a L:B ratio of 6:1. The total TO using $Cu(OPiv)_2$ (~100 TO, ~83% yield) is improved relative to $Cu(OAc)_2$ (~80 TO). These experiments revealed the potential importance of having a carboxylate group to achieve catalysis as only Cu(II) salts with carboxylate groups are effective (FIG. 2). Transition-metal carboxylates have been implicated in efficient arene C—H activation, and thus we tentatively conclude that the apparent necessity of Cu(II) carboxylate salts is partially due to their role in regenerating Rh carboxylates, which are likely integral for arene C—H activation. (Li, L.; Brennessel, W. W.; Jones, W. D. *Organometallics* 2009, 28, 3492) Furthermore, the effect of oxidant loading was investigated and revealed that increasing the oxidant:catalyst ratio increases rate of catalysis in a manner that is approximately first-order in oxidant revealing higher TO with increasing Cu(II) amounts (FIG. 3).

Figure 4A:
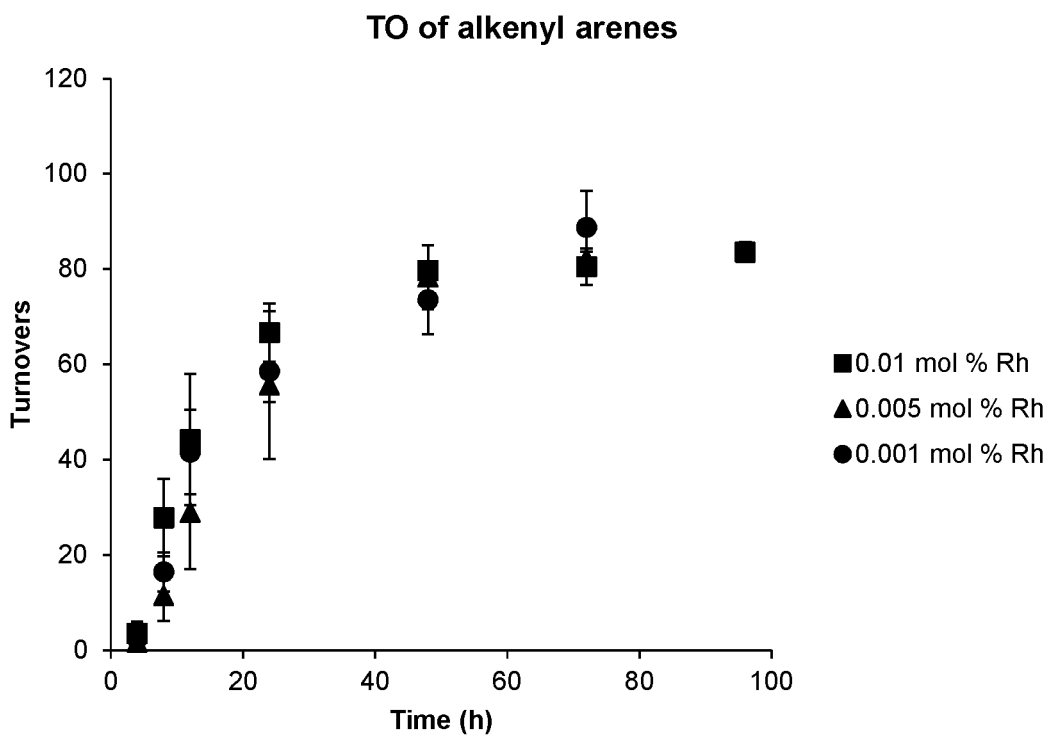
FIGS. 4A-4B shows the effect of rhodium loading (relative to benzene) on catalytic conversion of benzene and propylene using [Rh(μ-OAc)(η$^2$-C$_2$H$_4$)$_2$]$_2$ as a catalyst. Reaction conditions: 240 equivalents Cu(OAc)$_2$, 25 psig propylene, 150° C. Error bars represent standard deviations of at least three independent experiments.
Figure 4B:
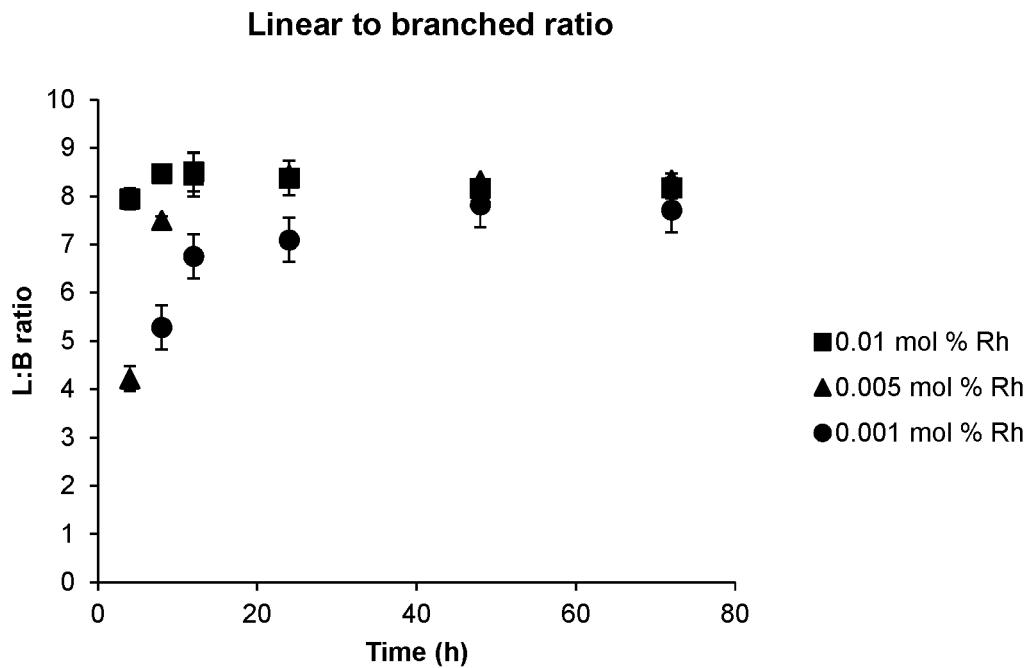
Figure 5:
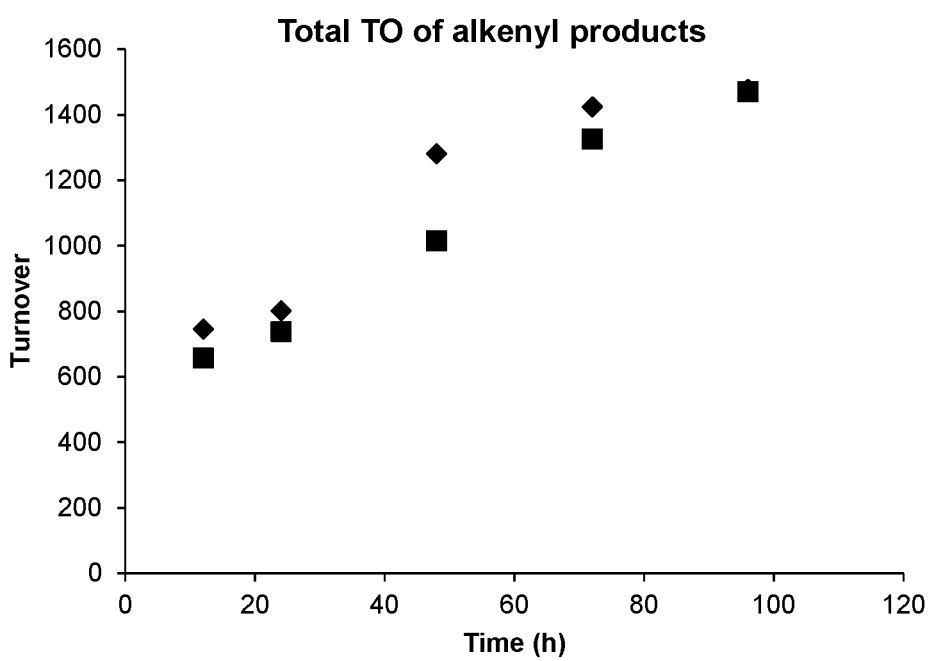
FIG. 5 shows the effect of high oxidant and low rhodium loading on functionalized benzene production using [Rh(μ-OAc)(η$^2$-C$_2$H$_4$)$_2$]$_2$ as a catalyst. Reaction conditions: 0.001 mol % Rh catalyst, 2400 equiv. Cu(OPiv)$_2$, 50 psig propylene. After the 48 hour sampling an additional 1200 equivalents of Cu(OPiv)$_2$ was added. Data for two independent runs are shown.
Figure 6:
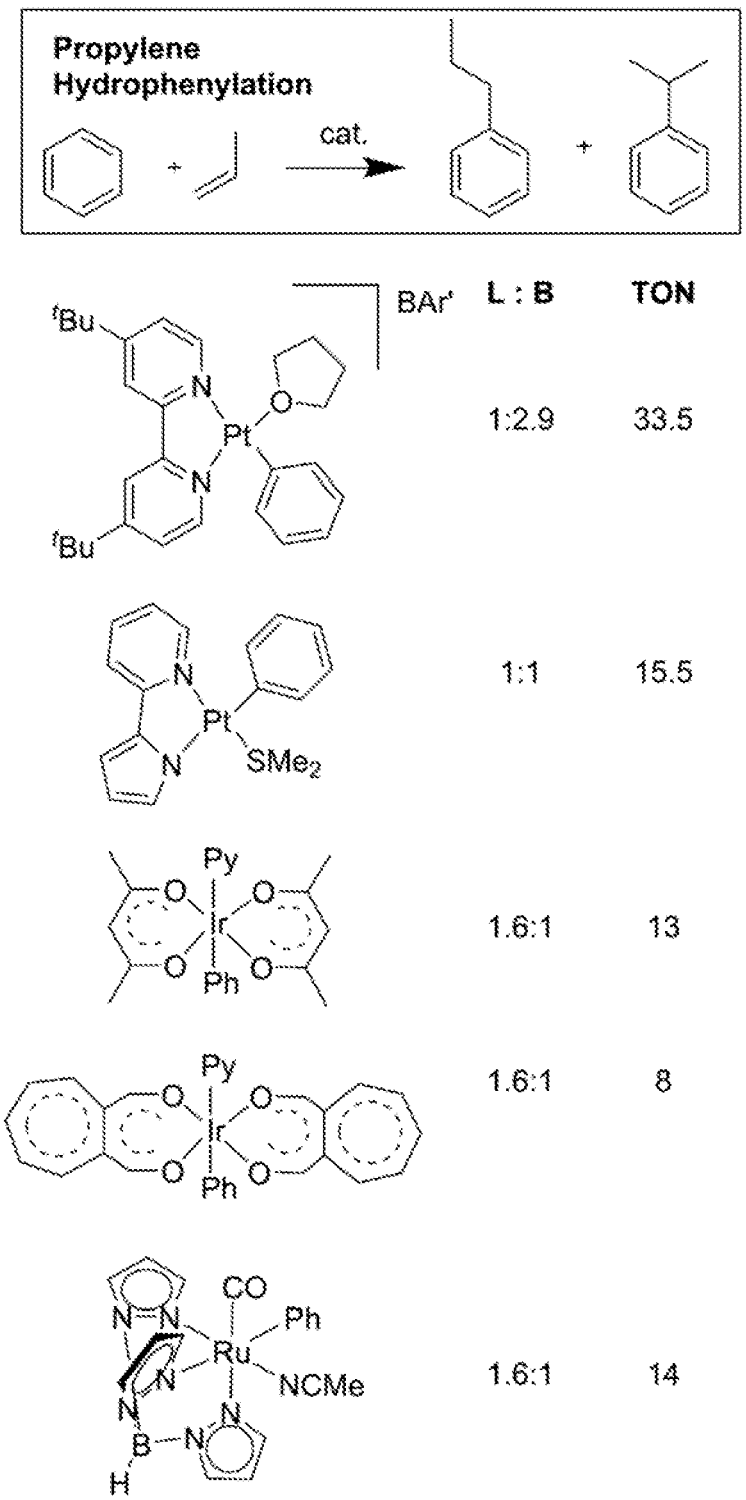
FIG. 6 shows selected catalysts that have been reported to catalyze the hydrophenylation of propene with observed selectivities and turnover number (TON). Linear:branched (L:B in the graphic) refers to ratio of n-propylbenzene to cumene.

The effect of temperature was examined (FIG. 1). At temperatures lower than 150° C., a negligible amount of catalytic activity is observed. The catalyst is stable and demonstrates increased catalytic activity at temperatures higher than 150° C., however, undesired side reactions become accessible. For example, small quantities of biphenyl (11(1) TO) and phenyl acetate (8(1) TO) are produced at 180° C., in addition to 84(12) TO of vinyl benzenes. The generation of phenyl acetate is a side reaction mediated by the Cu oxidant, as it is also observed when benzene and $Cu(OAc)_2$ are heated at 180° C. in the absence of olefin and Rh catalyst. (Webster-Gardiner, M. S.; Piszel, P. E.; Fu, R.;

McKeown, B. A.; Nielsen, R. J.; Goddard III, W. A.; Gunnoe, T. B. *J. Mol. Cat. A. Chem* 2017, 426, 379) We probed the impact of starting concentration of 1 on TO (FIG. 4). Performing catalysis over a concentration range from 0.01 to 0.001 mol % 1 (relative to benzene) revealed very little difference in TO versus time plots, and similar L:B selectivities were observed. The reaction appears to only be limited by the amount of oxidant. $Cu(OPiv)_2$ was investigated as the oxidant due to its solubility in benzene and thus experimental stirring challenges are relieved. For example, catalysis using 0.001 mol % of 1 with 2400 equivalents of $Cu(OPiv)_2$ led to 1148(133) TO of alkylated products after 48 hours, which corresponds to a 96% yield based on the limiting oxidant (FIG. 5). The addition of more oxidant (1200 eq to the reaction), before complete consumption of the initial oxidant, resulted in continued catalytic activity with a total of 1474(3) TO obtained after 96 hours for an overall 82% yield. Catalyst decomposition appears to occur after consumption of oxidant.

We probed catalysis using other olefins and arenes (Table 1) using a standard set of conditions {10 mL benzene, 0.01 mol % 1 (relative to benzene), 2000 equivalents of olefin (relative to 1) or 25 psig for gaseous olefins, and 240 equiv. $Cu(OAc)_2$ (relative to 1)}. The production of vinyl and allyl species was observed for all olefins except neohexene, for which allyl arene formation is not possible. Reported TO in Table 1 are based on analysis of hydrogenated products after the completion of catalytic reactions. For neohexene, only the 100% linear product (3,3-dimethylbutyl)benzene was observed [30(8) TO after 72 h]. With isobutylene, the vinyl and allyl anti-Markovnikov products were produced with 100% selectivity and hydrogenated to give isobutylbenzene [100(2) TO after 72 hours]. Hydrogenated samples from catalysis with 1-pentene gave 100% yield relative to oxidant and an ~8:1 ratio of linear (n-pentylbenzene, 110(10) TO) to branched (2-pentylbenzene, 12(3) TO) products after 72 hours. It is important to note that the reaction of 1-pentene can yield 1-pentyl or 2-pentyl products, while reaction with 2-pentene can generate 2-pentyl or 3-pentyl products. Therefore, the observation of minimal (<2 TO) 3-pentylbenzene production indicates that isomerization of 1-pentene to 2-pentene is slow, that reaction with 2-pentene is likely selective for the 2-pentyl product, and/or that the catalyst reacts more rapidly with 1-pentene than 2-pentene. Interestingly, utilizing the internal olefin 2-pentene produces 22(4) TO of n-pentylbenzene, 48(6) TO of 2-pentylbenzene with 27(5) TO of 3-pentylbenzene after hydrogenation. Starting with 2-pentene the amount of 1-pentene is likely low since it is thermodynamically disfavored. Thus, the formation of n-pentylbenzene starting from 2-pentene suggests that reaction of the catalyst with 1-pentene is likely more rapid that reaction with 2-pentene.

TABLE 1

Comparison of arene alkylation using $AlCl_3$ as the primary catalyst versus $[Rh(\mu-OAc)(\eta^2-C_2H_4)_2]_2$.

| Catalyst | Arene | Coupling Partner | o:m:p | L:B | TON |
|---|---|---|---|---|---|
| $AlCl_3$[*] | toluene | propylene | 3:1:2.6 | >98% B | n.r. |
| 1 | toluene | propylene | 1:8.9:9.3 | 9.4:1 | 86(17) |
| $AlCl_3$[£] | chlorobenzene | 2-chloropropane | 6.4:1:5.1 | 100% B | n.r. |
| 1 | chlorobenzene | propylene | 1:11:7 | 10:1 | 116(3) |
| $AlCl_3$[¤] | anisole | 2-chloropropane | 62:4:34 | 100% B | n.r. |
| 1 | anisole | propylene | 1:2.4:6.4 | 7.8:1 | 92(7) |
| $AlCl_3$[†] | benzene | propylene | n/a | 100% B | 95 |
| 1 | benzene | propylene | n/a | 8:1 | 80(4) |

TABLE 1-continued

Comparison of arene alkylation using AlCl₃ as the primary catalyst versus [Rh(μ-OAc)(η²-C₂H₄)₂]₂.

| Catalyst | Arene | Coupling Partner | o:m:p | L:B | TON | Product |
|---|---|---|---|---|---|---|
| AlCl₃[†] | benzene | 1-hexene | n/a | 100% B | 67 | |
| 1 | benzene | 1-pentene[§] | n/a | 8:1 | 122(10) | |
| 1 | benzene | 2-pentene | n/a | 1:3.4 | 97(10) | R = propyl |
| 1 | benzene | neohexene[§] | n/a | 100% L | 30(8) | |
| 1 | benzene | isobutylene[§] | n/a | 100% L | 100(2) | |
| AlCl₃[×] | benzene | isobutylene | n/a | 100% B | n.r. | |

Hydrogenation was achieved through 5% Pt on carbon under hydrogen atmosphere. L:B ratios and total TO of alkylated products determined after hydrogenation of unsaturated products. Unless otherwise noted, conditions are: 0.01 mol % Rh catalyst relative to arene, 25 psig gaseous olefin or 2000 equiv. of olefin, 150° C., 48 h, 240 equiv. Cu(OAc)₂ relative to Rh catalyst.
n.r. = not reported
[*]Data and conditions are from reference 31.
[£]Data and conditions are from reference 35.
[¤]Data and conditions are from reference 36.
[†]Data and conditions are from reference 19.
[§]72 h.
[×]Data and conditions are from reference 32.

In the absence of copper oxidant, complex 1 catalyzes rapid isomerization of 1-pentene to 2-pentene as conversion of 1-pentene to 2-pentene achieved equilibrium after at least 48 h (Table 2). In contrast, in the presence of Cu(OAc)₂, Cu(OTFA)₂, or Cu(OPiv)₂ the rate of isomerization of 1-pentene to 2-pentene by 1 is much slower. For example without added Cu(OAc)₂ after 72 h, only 12% 1-pentene remains whereas with 240 equiv. of Cu(OAc)₂ (relative to 1), 78% remains as 1-pentene after 72 h. The different rate of 1-pentene isomerization in the presence (slower) and absence (faster) of Cu(OAc)₂ suggests the possibility that a Rh—H intermediate could play a key role in the olefin isomerization. Cu(OAc)₂ might rapidly react with the Rh—H intermediate, which would compete with its ability to isomerize 1-pentene. It is interesting to note that catalysis with benzene and 2-pentene produces 22 TO of n-pentylbenzene but 1-pentene likely remains approximately 1% of the total pentene throughout catalysis. Thus, 1 appears to react more rapidly with 1-pentene than 2-pentene.

TABLE 2

Comparison of isomerization for 1-pentene, with and without Cu(OAc)₂, as well as the isomerization of 2-pentene with Cu(OAc)₂. Standard deviations are based on at least three independent experiments.

| Time (h) | 1-pentene | 2-pentene | Total Olefin | % 1-pentene | % 2-pentene |
|---|---|---|---|---|---|
| 1-Pentene isomerization with 240 equiv. of Cu(OAc)₂, equivalents of olefin | | | | | |
| 0 | 1885 (65) | 8 (0.6) | 1893 (64) | 99.6 | 0.4 |
| 48 | 1461 (44) | 280 (31) | 1741 (19) | 83.91 | 16.1 |
| 72 | 1246 (37) | 360 (38) | 1605 (19) | 77.6 | 77.6 22.4 |
| 1-Pentene isomerization without Cu(OAc)₂, equivalents of olefin | | | | | |
| 0 | 1856 (67) | 9.4 (2) | 1865 (66) | 99.5 | 0.5 |
| 48 | 258 (17) | 1669 (80) | 1927 (66) | 13.4 | 86.6 |
| 72 | 229 (13) | 1645 (50) | 1874 (39) | 12.2 | 87.8 |
| 2-Pentene isomerization with 240 equiv. of Cu(OAc)₂, equivalents of olefin | | | | | |
| 0 | 19 (1) | 2066 (60) | 2085 (61) | 0.93 | 99.07 |
| 48 | 24 (2) | 1654 (134) | 1678 (135) | 1.43 | 98.57 |
| 72 | 25 (2) | 1562 (117) | 1588 119) | 1.59 | 98.41 |

TABLE 2-continued

Comparison of isomerization for 1-pentene, with and without Cu(OAc)$_2$, as well as the isomerization of 2-pentene with Cu(OAc)$_2$. Standard deviations are based on at least three independent experiments.

| Time (h) | 1-pentene | 2-pentene | Total Olefin | % 1-pentene | % 2-pentene |
|---|---|---|---|---|---|
| 1-Pentene isomerization with 240 equiv. of Cu(TFA)$_2$, equivalents of olefin | | | | | |
| 0 | 1810 (32) | 14 (3) | 1823 (33) | 99.2 | 0.8 |
| 48 | 1717 (120) | 93 (16) | 1810 (68) | 94.0 | 5.1 |
| 72 | 1688 (82) | 114 (16) | 1803 (55) | 93.7 | 6.3 |
| 1-Pentene isomerization with 240 equiv. of Cu(OPiv)$_2$, equivalents of olefin | | | | | |
| 0 | 1699 (39) | 1.4 (0.05) | 1700 (36) | 99.9 | 0.1 |
| 48 | 632 (216) | 850 (216) | 1482 (42) | 42.7 | 57.3 |
| 72 | 554 (278) | 949 (281) | 1503 (50) | 36.9 | 63.1 |

The efficacy and selectivity of acid-based arene alkylation varies dramatically with arene substrate, and selectivity is typically dictated by directing group effects. But, catalysis using 1 appears to be broadly applicable to different types of arenes with selectivity appearing to be catalyst-driven. Table 1 shows the results using AlCl$_3$ and complex 1 for several arenes and olefins (note: the selectivities in Table 1 are determined after hydrogenation using 5% Pt on carbon to yield saturated alkyl substituents). For AlCl$_3$ catalyzed alkylation, electron-deficient arenes react substantially slower, often not at all. For example, the rate of chlorobenzene alkylation (AlCl$_3$ with propylene in nitromethane at 25° C.) is approximately 10 times slower relative to benzene with a product distribution of ortho:meta:para (o:m:p) of ~11:1:8. (Röper, M.; Gehrer, E.; Narbeshuber, T.; Siegel, W. In *Ullmann's Encyclopedia of Industrial Chemistry*; Wiley-VCH Verlag GmbH & Co. KGaA: 2000; Olah, G. A.; Flood, S. H.; Kuhn, S. J.; Moffatt, M. E.; Overchuck, N. A. *J. Am. Chem. Soc.* 1964, 86, 1046; Olah, G. A.; Flood, S. H.; Moffatt, M. E. *J. Am. Chem. Soc.* 1964, 86, 1060) In contrast, using AlCl$_3$, electron-rich arenes react faster relative to benzene. (Germain, J. E. Catalytic conversion of hydrocarbons; Academic Press: London, 1969) Using AlCl$_3$ as a catalyst, toluene alkylation with propylene (AlCl$_3$ in nitromethane at 25° C.) produces an unselective o:m:p ratio of 3:1:2.6. (Olah, G. A.; Flood, S. H.; Kuhn, S. J.; Moffatt, M. E.; Overchuck, N. A. *J. Am. Chem. Soc.* 1964, 86, 1046) Using standard conditions with 1, catalysis with chlorobenzene gave 116(3) TO (97% yield) of alkyl chlorobenzene with a L:B ratio of 10:1 and o:m:p ratio of 1:11:7. Toluene and anisole were investigated as representative electron-rich arenes to evaluate catalytic activity. The reaction of toluene and propylene gave 86(17) TO (72% yield) of alkyl toluene, L:B ratio of 9.4:1, and an o:m:p ratio of 1:8.9:9.3. Anisole gave 92(7) TO (77% yield) of alkyl anisole, L:B of 7.8:1, and an o:m:p ratio of 1:2.4:6.4. Catalysis using 1 reveals an unusually high selectivity towards meta products, which could provide routes to new or difficult to access compounds. Further, the anisole results are particularly intriguing because the para products are estragole (allyl) and anethole (vinyl), which are common materials in the flavors and fragrance industries. (Fahlbusch, K.-G.; Hammerschmidt, F.-J.; Panten, J.; Pickenhagen, W.; Schatkowski, D.; Bauer, K.; Garbe, D.; Surburg, H. In Ullmann's Encyclopedia of Industrial Chemistry; Wiley-VCH Verlag GmbH & Co. KGaA: 2000.)

For all the aromatic substrates evaluated, catalysis using 1 provides alternative selectivity to traditional acid-based methods. The arene electronics have a negligible impact on TO and the rate of reaction. Table 1 shows comparisons between acid-based catalysis (AlCl$_3$) and the results using Rh precatalyst 1. The o:m:p ratios highlight the differences between rhodium-mediated catalysis and acid-based catalysis. For rhodium-mediated catalysis using 1 the relative TO is comparable to benzene reactivity and the o:m:p ratio favors meta and para functionalization, regardless of benzene functionality, presumably based on the regioselectivity of Rh-mediated C—H activation. (Jones, W. D. *Inorg. Chem.* 2005, 44, 4475.) In addition, the rhodium precatalyst 1 generates the vinyl and allyl products for each product in an approximate 1:1 ratio. In contrast, AlCl$_3$, a typical Friedel-Crafts catalyst, generates only saturated products and is highly selective in all cases for branched product.

To our knowledge, there are no previous examples of catalytic conversion of simple arenes and α-olefins, such as propylene, 1-pentene, 1-hexene, etc., to alkyl or vinyl/allyl products with high selectivity for anti-Markovnikov products. Herein, we have reported that a simple Rh(I) catalyst precursor, easily generated from commercially available materials, achieves such transformations. (Cramer, R.; McCleverty, J. A.; Bray, J. In *Inorganic Syntheses*; John Wiley & Sons, Inc.: 2007, p 86; Werner, H.; Poelsma, S.; Schneider, M. E.; Windmüller, B.; Barth, D. *Chem. Ber.* 1996, 129, 647) Such catalysis opens the door to a range of previously inaccessible products using common petrochemicals. Furthermore, the catalytic process is effective for benzene substituted with electron donating or withdrawing groups with ortho/meta/para selectivity that is unique from acid-based catalysis. The range of arene and olefin scope allows for the generation of previously synthetically challenging materials using air-recyclable Cu(II) oxidants.

Example 2

Figure 7:
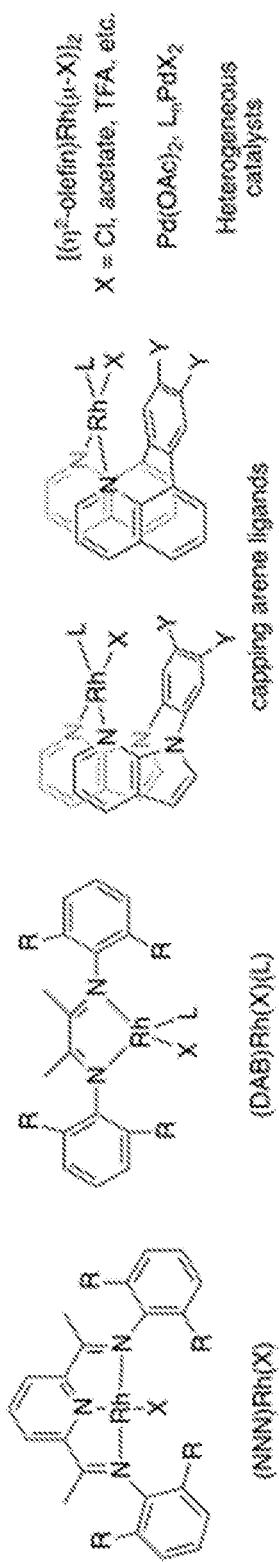
FIG. 7 shows examples of catalysts that convert toluene and pentenes or hexenes to straight-chain alkenyl or alkyl arenes (X=anionic ligand such as acetate, trifluoroacetate, halide; R and Y are various substituents such as alkyl, aryl, halide, ether, amine, etc., L=neutral ligand such as a nitrile or olefin).

The selective production of super linear alkyl and alkenyl arenes can be accomplished with metal-complex catalysts. Examples of catalysts that we have demonstrated successful are shown in FIG. 7 and include Rh complexes with tridentate and bidentate ligands, Rh complexes with N-based ligands with "capping arenes" (such as the diquinoline based and related ligands), simple Rh salts, Pd salts and heterogeneous variants of these homogeneous catalysts. We have demonstrated selective conversion of toluene and 1-pentene to linear 1-substituted pentenyl toluenes with high selectivity, 1- to 2-pentyl toluene selectivity up to 15:1 and 1-+2-pentyl toluenes to 3-pentyl toluenes >30:1. In general, the processes are selective for meta and para over ortho. Similar results have been obtained with 1-hexene. Also, starting with 2-pentene or 2-hexene, substantial amounts of 1-alkenyl toluenes are produced, often in a near 1:1 ratio with 2-alkenyl toluenes. Starting with 2-pentene or 2-hexene, ratios of 1-+2-alkenyl toluenes to 3-alkenyl toluenes that favor 1-/2- have been achieved. Thus, a process that uses a mixture of pentene or hexene isomers is viable.

Using [Rh(m-OAc)$_2$(C$_2$H$_4$)$_2$]$_2$ to convert toluene and 1-pentene produces pentenyltoluenes as well as tolyl acetates and C$_{10}$ products. In each case, the production of 1-pentenyltoluenes is heavily favored over 2-pentenyltoluenes whereas the production of 3-pentenyltoluenes is trace at most. For example, one set of conditions gives a 1-:2-:3-pentenyltoluene ratio of 28:3.6:1. The use of 2-pentene as the olefin source has also been examined, and a substantial amount of 1-pentenyl was produced with, for example, a 1-:2-:3-pentenyltoluene ratio of 1:3.5:2.2. In all cases the meta- and para-pentenyltoluenes are heavily favored over the ortho products, with an m:p:o ratio of 43:32:1 for a representative reaction (for all Rh catalysts).

Since hexenyltoluenes can also be used in the synthesis of PEN, the reactions of toluene and 1- or 2-hexene with [Rh(μ-OAc)$_2$(C$_2$H$_4$)$_2$]$_2$ have also been studied. With 1-hexene, the product ratio strongly favors linear hexenyltoluenes with a 1-:2-:3-hexenyltoluene ratio of 8.4:1.6:1. With 2-hexene, similar to the case with 2-pentene, the product distribution is 1-:2-:3-hexenyltoluenes of 1:2.0:1.9.

Using capping arene Rh catalysts (e.g. FIG. 7) for the conversion of 1-pentene and toluene, the selectivity for linear pentenyltoluenes is increased; for example the distribution of 1-:2-:3-pentenyltoluene of 30:2:1 is observed (a 15:1 1-pentenyl to 2-pentenyl ratio).

The Cu(II) salts can be regenerated using air or purified oxygen. Two processes have been demonstrated, one example of Cu(II) recycling is accomplished by stirring of the catalyst solution in air at room temperature and then removing air and adding olefin; in a second example the catalyst solution is heat with air (e.g., at approximately 150° C.) followed by removal of air and addition of olefin if necessary. Preliminary results also indicate that the addition of acid (such as acetic or pivalic acid can facilitate Cu(II) regeneration and improve catalyst longevity. For example, in one case we have demonstrated a Rh catalyst that is active and shows no signs of decomposition for >200 hours.

The process works with other metal catalysts, such as Pd(OAc)$_2$ as well as example of Pd(II) ligated by mono-, bi- and tridentate ligands, although selectivities are altered. The process works with heterogeneous catalysts. In one example, Rh nanoparticles on silica converts toluene and 1-pentene to pentenyl toluenes with a 1-pentenyl to 2-pentyl ratio of approximately 15:1 (there is no detectable formation of 3-pentenyl toluenes). The selectivity for meta+para is >90%.

The synthesis of DMN can be implemented through a multi-step process involving initial synthesis of pentenyl or hexenyl toluenes followed by catalytic dearomatization to form DMN. Alternatively, a one-step tandem catalytic process that uses compatible catalysts that converts toluene and pentene or hexene to DMN or MEN, respectively, can be used.

Example 3. Conversion of Benzene and Ethylene to Styrene

Example 3.1

Using Rh(μ-TFA)(5-FP) (5-FP=1,2-bis(N-7-azaindoly) benzene; TFA=trifluoroacetate) as the catalyst, we can achieve over 95% yield (based on Cu oxidant) under different conditions. In this reaction, the loading of Rh complex is 0.001 mol % (relative to benzene) and 240 eq. Cu(II) salts (relative to Rh, Cu(OPiv)$_2$ or Cu(OAc)$_2$) are added as the in situ oxidant. The reaction is carried out in neat benzene with ethylene as the only olefin source. Styrene is the main product and trace amounts of phenyl acetate/pivalate, biphenyl and trans-stilbene are detected as side products. The reaction can achieve over 95% yield of styrene at various temperatures (from 120-150° C.) and ethylene pressures (from 15-75 psig). When using 2400 eq. Cu(II) salts (relative to Rh) as the oxidant, over 700 TOs can be achieved. When increasing the ethylene pressure to 500 psig, we can achieve over 99:1 selectivity for styrene over trans-stilbene.

Example 3.2

A 10 mL benzene solution of ($^{FI}$DAB)Rh(TFA)(η$^2$-C$_2$H$_4$) [$^{FI}$DAB=N,N'-bis(pentafluorophenyl)-2,3-dimethyl-1,4-diaza-1,3-butadiene; TFA=trifluoroacetate] (0.0001 mol % Rh relative to benzene) was treated with 75 psig ethylene, 2400 equiv. Cu(OAc)$_2$ and heated to 150° C. Styrene TON of 817-852 were obtained after 96 h.

Example 3.3

With 0.001 mol % Rh (Rh source=[Rh(μ-OAc)(C$_2$H$_4$)$_2$]$_2$) relative to 10 mL benzene, under 40 psig of propylene with Cu(OAc)$_2$ (240 equiv. relative to Rh) at 150° C. for 20 h, 114(3) TO of styrene was obtained, corresponding to ~95% yield relative to Cu(OPiv)$_2$.

Example 3.4

Heating a 10 mL benzene solution of ($^{FI}$NNN)Rh(TFA) [$^{FI}$NNN=2,6-diacetylpyridine-bis(pentafluoroaniline)] (0.001 mol % Rh relative to benzene) to 150° C. under 40 psig of ethylene with Cu(OAc)$_2$ (240 equiv. relative to Rh) over 48 h gives 110(4) TO of styrene, corresponding to ~92% yield relative to Cu(OAc)$_2$.

Example 4. Conversion of Benzene and α-Olefins to Alkenyl and Vinyl Arenes

Example 4.1

Using Rh(μ-TFA)(5-FP) [5-FP=1,2-bis(N-7-azaindoly) benzene] as the catalyst for this transformation, we can achieve over 75% yield (based on Cu oxidant) with a linear:branched ratio of up to 18:1 under optimized conditions (linear:branched ratio refers to ratio of 1- and higher substituted aryl alkanes upon hydrogenation of the alkenuyl arene). In this reaction, the loading of Rh complex is 0.001 mol % (relative to benzene) and 240 eq. Cu(II) salts (relative to Rh, Cu(OPiv)$_2$ or Cu(OAc)$_2$) are added as the in situ oxidant. The reaction is carried out in neat benzene with propylene as the olefin. Production of linear vinylbenzenes (e.g., allybenzene, β-cis-methylstyrene, β-trans-methylstyrene) dominates over branched vinylbenzene (e.g., α-methylstyrene). Phenyl pivalate and biphenyl are detected as side products in trace amounts. The reaction can achieve over 70% yield at various temperatures (from 120-150° C.) with linear products being more favored at lower temperatures. When using 2400 eq. of Cu(II) salts (relative to Rh) as the oxidant, over 900 TOs can be achieved.

Example 4.2

Heating a 10 mL benzene solution of ($^{FI}$DAB)Rh(OAc)(η$^2$-C$_2$H$_4$) [$^{FI}$DAB=N,N'-bis(pentafluorophenyl)-2,3-dimethyl-1,4-diaza-1,3-butadiene; OAc=acetate] (0.001 mol % Rh relative to benzene) to 150° C. under 25 psig of propylene with Cu(OPiv)$_2$ (240 equiv. relative to Rh) over 2 hours affords propenylbenzene products with a linear:branched ratio of 9:1. The total TO of alkenyl benzenes products were ~60, corresponding to ~50% yield relative to Cu(OPiv)$_2$.

Example 4.3

Heating a 10 mL benzene solution of ($^{FI}$DAB)Rh(OAc)(η$^2$-C$_2$H$_4$) [$^{FI}$DAB=N,N'-bis(pentafluorophenyl)-2,3-dimethyl-1,4-diaza-1,3-butadiene; OAc=acetate] (0.001 mol % Rh relative to benzene) to 150° C. with 2000 equiv. 1-pentene and 240 equiv. Cu(OPiv)$_2$ for 2 hours affords an ~10:1 ratio of linear (n-pentylbenzene, 105(6) TO) to branched (2-pentylbenzene, 10(1) TO) products following hydrogenation with Pt/C.

Example 4.4

Heating a 10 mL benzene solution of $(^{FI}DAB)Rh(OAc)(\eta^2-C_2H_4)$ [$^{FI}DAB=N,N'$-bis(pentafluorophenyl)-2,3-dimethyl-1,4-diaza-1,3-butadiene; OAc=acetate] (0.001 mol % Rh relative to benzene) to 150° C. with 2000 equiv. 2-pentene and 240 equiv. $Cu(OPiv)_2$ for 2 hours produces 13(1) TO of n-pentylbenzene, 52(4) TO of 2-pentylbenzene with 29(2) TO of 3-pentylbenzene following hydrogenation with Pt/C.

Example 4.5

With 0.0001 mol % Rh (Rh source=$[Rh(\mu$-OAc$)(C_2H_4)_2]_2$) relative to 10 mL benzene, under 25 psi of propylene with $Cu(OPiv)_2$ (240 equiv. relative to Rh) at 150° C. for 48 h, an ~8:1 ratio of linear:branched products and 1148(133) TO of alkenyl products were obtained.

Example 4.6

With 0.001 mol % Rh (Rh source=$[Rh(\mu$-OAc$)(C_2H_4)_2]_2$) relative to 10 mL benzene, 2000 eq. 1-pentene and 240 eq. $Cu(OAc)_2$ under anaerobic conditions at 150° C. for 72 h, an ~8:1 ratio of linear (n-pentylbenzene, 110(10) TO) to branched (2-pentylbenzene, 12(3) TO) products were obtained following hydrogenation using Pt/C.

Example 4.7

With 0.001 mol % Rh (Rh source=$[Rh(\mu$-OAc$)(C_2H_4)_2]_2$) relative to 10 mL benzene, 2000 eq. 2-pentene and 240 eq. $Cu(OAc)_2$ under anaerobic conditions at 150° C. for 72 h, 22(4) TO of n-pentylbenzene, 48(6) TO of 2-pentylbenzene with 27(5) TO of 3-pentylbenzene were obtained after hydrogenation with Pt/C.

Example 4.8

A 10 mL benzene solution of $(^{FI}NNN)Rh(TFA)$ [$^{FI}NNN$=2,6-diacetylpyridine-bis(pentafluoroaniline)] (0.001 mol % Rh relative to benzene) was charged with 25 psig propylene, 240 equiv. $Cu(OAc)_2$ and heated to 150° C. for 72 h. An ~8:1 ratio of linear to branched products and 94(8) TO of alkenyl products were obtained

Example 4.9

A 10 mL benzene solution of $(^{FI}NNN)Rh(TFA)$ [$^{FI}NNN$=2,6-diacetylpyridine-bis(pentafluoroaniline)] (0.001 mol % Rh relative to benzene) was treated with 2000 equiv. of 1-pentene, 240 equiv. $Cu(OAc)_2$ and heated to 150° C. for 72 h. A ~10:1 ratio of linear (n-pentylbenzene, 110(14) TO) to branched (2-pentylbenzene, 11(1) TO) products were obtained following hydrogenation using Pt/C.

Example 4.10

A 10 mL benzene solution of $(^{FI}NNN)Rh(TFA)$ [$^{FI}NNN$=2,6-diacetylpyridine-bis(pentafluoroaniline)] (0.001 mol % Rh relative to benzene) was treated with 2000 equiv. of 2-pentene, 240 equiv. $Cu(OAc)_2$ and heated to 150° C. for 72 h. 25(2) TO of n-pentylbenzene, 53(7) TO of 2-pentylbenzene with 25(2) TO of 3-pentylbenzene were obtained after hydrogenation using Pt/C.

Example 4.11

A solution containing $[Rh(\mu$-OAc$)(\eta^2-C_2H_4)_2]_2$ (0.005 g, 0.012 mmol, 0.001 mol % of rhodium relative to benzene), hexamethylbenzene (0.075 g, 0.45 mmol), and benzene (200 mL) was prepared in a volumetric flask. Fisher-Porter reactors were charged with 10 mL of the Rh stock solution and $Cu(OAc)_2$ (0.050 g, 0.28 mmol). The vessels were sealed, neohexene added, and subsequently stirred and heated to 150° C. Analysis of products revealed alkenylation with quantitative selectivity for the linear product (i.e., 3,3-dimethylbutyl)benzene).

Example 4.12

A solution containing $[Rh(\mu$-OAc$)(\eta^2-C_2H_4)_2]_2$ (0.005 g, 0.012 mmol, 0.001 mol % of rhodium relative to benzene), hexamethylbenzene (0.075 g, 0.45 mmol), and benzene (200 mL) was prepared in a volumetric flask. Fisher-Porter reactors were charged with 10 mL of the Rh stock solution and $Cu(OAc)_2$ (0.050 g, 0.28 mmol). The vessels were sealed, isobutylene added, and subsequently stirred and heated to 150° C. Analysis of products revealed alkenylation with quantitative selectivity for the linear products (i.e., sole formation of 2-methylpropyl benzene after hydrogenation).

Example 5. Conversion of Toluene and Olefins to Disubstituted Arene Products

Example 5.1

With 0.01 mol % Rh (Rh source=$[Rh(\mu$-OAc$)(C_2H_4)_2]_2$) relative to 10 mL toluene, 1000 eq. 1-pentene and 480 eq. $Cu(OAc)_2$ under anaerobic conditions, ~60 TO of pentyltoluenes were obtained following hydrogenation using Pt/C after reaction at 150° C. for 96 h. Of the pentyltoluene products, 87% are m-n-pentyltoluene or p-n-pentyltoluene.

Example 5.2

With 0.01 mol % Rh (Rh source=$[Rh(\mu$-OAc$)(C_2H_4)_2]_2$) relative to 10 mL toluene, 1000 eq. 1-pentene and 240 eq. $Cu(OAc)_2$ under anaerobic conditions at 150° C. for 72 h, $C_{10}$ products account for approximately 5% of the total products. Products were analyzed following hydrogenation with Pt/C to reveal selectivity for m-n-pentyltoluene and p-n-pentyltoluene.

Example 5.3

With 0.01 mol % Rh (Rh source=$[Rh(\mu$-OAc$)(C_2H_4)_2]_2$) relative to 10 mL toluene, 500 eq. 1-pentene and 240 eq. $Cu(OAc)_2$ under aerobic or anaerobic conditions at 150° C. for 96 h, selectivity for meta and para products were ~50% and ~45%, respectively for both cases. Samples were hydrogenated using Pt/C, and ~70 TO of pentyltoluenes were obtained. N-pentyltoluene was the dominant product, accounting for ~85% of pentyltoluenes. 2-Pentyltoluene accounted for ~10% of pentyltoluenes.

Example 5.4

With 0.01 mol % Rh(TFA)(5-FP) (5-FP=1,2-bis(N-7-azaindoly)benzene) relative to 10 mL toluene, 500 eq. 1-pentene and 240 eq. $Cu(OAc)_2$ or $Cu(OPiv)_2$ under anaerobic conditions, there was a significant difference in TO based on the identity of the Cu(II) salt. The reaction mixtures were hydrogenated after 96 h at 150° C. With $Cu(OAc)_2$, 52(3) TO of pentyltoluenes were obtained, while 159(3) TO of pentyltoluenes were obtained with $Cu(OPiv)_2$. However, there no major differences in selectivity based on the identity of the Cu(II) salt, with n-pentyltoluene accounting for ~90% of pentyltoluene products in each case. Meta and para products were also dominant (~50% for each with Cu(OAc)$_2$ and ~60% and ~40%, respectively, for Cu(OPiv)$_2$).

Example 5.5

With 0.01 mol % Rh(TFA)(5-FP) (5-FP=1,2-bis(N-7-azaindoly)benzene) relative to 20 mL toluene, 2000 eq. 1-pentene and 600 eq. Cu(OPiv)$_2$ under anaerobic conditions, >80% yield, based on Cu(II) oxidant, is obtained after 48 h at 150° C. Reaction mixtures were hydrogenated using Pt/C. N-pentyltoluene accounts for ~90% of pentyltoluenes, and meta and para pentyltoluenes account for ~60% and ~40%, respectively with <1% ortho products.

Example 5.6

With 0.01 mol % Rh (Rh source=[Rh(μ-OAc)(C$_2$H$_4$)$_2$]$_2$) relative to 10 mL toluene, 500 eq. 2-pentene and 240 eq. Cu(OAc)$_2$ under anaerobic conditions at 150° C. for 96 h, ~15% of the pentyltoluenes observed following hydrogenation with Pt/C are n-pentyltoluene. 2-pentyltoluene accounts for 52% and 3-pentyltoluene is the remaining 33%.

Example 5.7

The addition of 240 eq. pivalic acid to a reaction mixture of 0.01 mol % Rh(TFA)(5-FP) (5-FP=1,2-bis(N-7-azaindoly)benzene) relative to 10 mL toluene, 500 eq. 1-pentene and 480 eq. Cu(OPiv)$_2$ under anaerobic conditions enhanced catalysis. Approximately 230 TO of pentyltoluenes were observed with the addition of pivalic acid, while ~180 TO were observed without added pivalic acid.

Example 5.8

With 0.01 mol % Rh(TFA)(5-FP) (5-FP=1,2-bis(N-7-azaindoly)benzene) relative to 10 mL toluene, 500 eq. 1-pentene and 480 eq. Cu(OPiv)$_2$ under anaerobic conditions at 150° C. for 240 h, >400 TOs of pentyltoluenes were obtained following hydrogenation with Pt/C. At each sampling point, the Cu(I) was recycled by adding 1 atm of air and heating for 20 min at 150° C. N-pentyltoluenes accounted for >90% of pentyltoluene products.

Example 5.9

With 0.01 mol % Rh (Rh source=[Rh(μ-OAc)(C$_2$H$_4$)$_2$]$_2$) relative to 10 mL toluene, 500 eq. 1-hexene and 240 eq. Cu(OAc)$_2$ under anaerobic conditions at 150° C. for 96 h, 66 TO of hexyltoluenes are obtained after 96 h following hydrogenation with Pt/C. N-hexyltoluene accounts for 76% of hexyltoluene products, with 15% and 9% 2-hexyltoluene and 3-hexyltoluene, respectively.

Example 5.10

With 0.01 mol % Rh (Rh source=[Rh(μ-OAc)(C$_2$H$_4$)$_2$]$_2$) relative to 10 mL toluene, 500 eq. 2-hexene and 240 eq. Cu(OAc)$_2$ under anaerobic conditions at 150° C. for 96 h, 65 TO of hexyltoluenes are obtained after 96 h following hydrogenation with Pt/C. 2-Hexyltoluene and 3-hexyltoluene account for the majority of products, with 41% and 39%, respectively. N-hexyltoluene accounts for 21%.

Example 6. Examples of Rh(II), Rh(III) and Heterogeneous Catalysts (Rh Nanoparticles and Zeolite Materials)

Example 6.1

Using 5 wt % Rh on SiO$_2$ as the catalysts for styrene synthesis, we can achieve 70% yield (based on Cu(II) oxidant) under different conditions. In this reaction, the loading of Rh/SiO$_2$ is 8 mg (0.00288 mmol Rh), and 77 mg Cu(OPiv)$_2$ (100 eq. Cu(II) salt relative to Rh) are added as the in situ oxidant. The reaction is carried out in neat benzene with ethylene at 150° C. Styrene is the main product with small amounts of phenyl pivalate, biphenyl and trans-stilbene detected as side products. The selectivity of styrene is 92%. With the addition of various amount of pivalic acid, a relatively higher yield (92%) and higher styrene selectivity (98%) are achieved.

Example 6.2

Using 1 wt % Rh on Al$_2$O$_3$ as the catalyst, >90% yield (based on Cu(II) oxidant) of styrene is observed. In this reaction, the loading of Rh/Al$_2$O$_3$ is 40 mg (0.00288 mmol Rh), and 77 mg Cu(OPiv)$_2$ (100 eq. Cu(II) salt relative to Rh) are added as the in situ oxidant. The reaction is carried out in neat benzene with ethylene at 150° C. Styrene is the main product and small amounts of phenyl pivalate is detected as side products. The selectivity for styrene is 98%.

Example 6.3

In this reaction, the loading of Rh/SiO$_2$ is 8 mg (0.00288 mmol Rh), and 77 mg Cu(OPiv)$_2$ (100 eq. Cu(II) salt relative to Rh) and 29.4 mg pivalic acid (100 eq. HOPiv relative to Rh) are added as the in situ oxidant. The reaction is carried out in neat benzene with propylene at 150° C. Allylbenzene is the main product with small amounts of β-cis-methylstyrene, β-trans-methylstyrene, and α-methylstyrene detected as side products. The selectivity for linear products (allylbenzene, β-cis-methylstyrene and β-trans-methylstyrene) is 91%. Without the addition of acid, Rh/SiO$_2$ catalysts achieved similar overall yield and selectivity for linear products.

Example 6.4

5 wt % Rh on SiO$_2$ can be used as the catalyst for aerobic styrene synthesis. In this reaction, the loading of Rh on SiO$_2$ is 8 mg (0.00288 mmol Rh), and 77 mg Cu(OPiv)$_2$ (100 eq. Cu(II) salt relative to Rh catalysts) are added as the in situ oxidant. In the presence of air, the reaction is carried out in neat benzene with ethylene at 150° C. Styrene is the main product and small amounts of phenyl pivalate, stilbene and biphenyl are detected as side products.

Example 6.5

Using 5 wt % Rh on SiO$_2$ as the catalysts for pentene alkenylation reaction, we can achieve 65% yield (based on Cu(II) oxidant). In this reaction, the loading of Rh/SiO$_2$ is 8 mg (0.00288 mmol Rh), and 77 mg Cu(OPiv)$_2$ (100 eq. Cu(II) salt relative to Rh) are added as the in situ oxidant. The reaction is carried out in neat benzene with 1-pentene at 150° C. The products are hydrogenated using Pt/C to quantify the linear and branched products selectivity. 1-Phenyl-pentane is the main product and small amounts of 2-phenylpentane and 3-phenylpentane are detected as side products. The selectivity for linear products (1-phenylpentane) is 90%.

Example 6.6

The loading of Rh/SiO$_2$ is 8 mg (0.00288 mmol Rh), and 77 mg Cu(OPiv)$_2$ (100 eq. Cu(II) salt relative to Rh) are added as the in situ oxidant. The reaction is carried out in neat toluene with 1-pentene at 150° C. The products are hydrogenated using Pt/C to quantify the selectivity for linear and branched products. n-Pentyltoluene is the primary product and small amounts of 2-pentyltoluenes are detected as side products. Selectivity for linear products (n-phenylpentane) is 94%. The selectivity for n-pentyltoluene is 54% for meta, 38% for para and 1% for ortho.

Example 6.7

In this reaction, the loading of Rh-ZSM-5 is 52 mg (0.0025 mmol Rh), and 60 mg Cu(OPiv)$_2$ (92 eq. Cu(II) salt relative to Rh) are added as the in situ oxidant. The reaction is carried out in neat benzene with ethylene at 150° C. Styrene is the main product. Different amounts of phenyl pivalate and ethylbenzene are detected as side products. The selectivity for styrene is 72%.

Example 6.8

In this reaction, the loading of Rh$_2$(OAc)$_4$ is 10 mg (0.0226 mmol Rh$_2$(OAc)$_4$), and 100 mg Cu(OPiv)$_2$ (16.6 eq. Cu(II) salt relative to Rh(II) catalysts) are added as the in situ oxidant. In the presence of air (1 atm), the reaction is carried out in neat benzene with ethylene at 150° C. Styrene is the main product and small amounts of vinyl pivalate, stilbene and biphenyl are detected as side products. The selectivity for styrene is 62%.

Example 6.9

Using Rh$_2$(OAc)$_4$ as the catalyst for propylene alkenylation reaction, we can achieve 89% yield (based on Cu(II) oxidant) under different conditions. In this reaction, the loading of Rh$_2$(OAc)$_4$ is 5 mg (0.0113 mmol Rh$_2$(OAc)$_4$), and 77 mg Cu(OPiv)$_2$ (25.6 eq. Cu(II) salt relative to Rh(II)) and 0.3 g pivalic acid are added as the in situ oxidant. In the presence of air, the reaction is carried out in neat benzene with propylene at 150° C. Allylbenzene and β-trans-methylstyrene are the main products with small amounts of β-cis-methylstyrene and α-methylstyrene detected as side products. Selectivity for linear products (allylbenzene, β-cis-methylstyrene and β-trans-methylstyrene) is 88%. Without added acid, it achieves similar overall product yield and selectivity towards linear products.

Example 6.10

In this reaction, the loading of Rh$_2$(OAc)$_4$ is 0.6 mg (0.00288 mmol Rh), and 77 mg Cu(OPiv)$_2$ (100 eq. Cu(II) salt relative to Rh) and 29.4 mg pivalic acid (100 eq. HOPiv relative to Rh) are added as the in situ oxidant. The reaction is carried out in neat benzene with propylene at 150° C. Allylbenzene is the main product with amounts of β-cis-methylstyrene, β-trans-methylstyrene, and α-methylstyrene detected as side products. Selectivity for linear products (allylbenzene, β-cis-methylstyrene and β-trans-methylstyrene) is 93%. Lowering the reaction temperature from 150° C. to 90° C., the linear products selectivity slightly increases from 93% to 95%.

Example 6.11

A 10 mL benzene solution of rhodium(III) acetate [hexakis(acetato)triaquo-μ-oxotrirhodium(III) acetate] (0.001 mol % Rh relative to benzene) was treated with 40 psig ethylene, 240 eq. Cu(OAc)$_2$ and heated to 150° C. for 24 hours to give 111 TO of styrene, corresponding to ~92% yield relative to Cu(OAc)$_2$.

Example 6.12

Heating a 10 mL benzene solution of rhodium(III) acetate [hexakis(acetato)triaquo-μ-oxotrirhodium(III) acetate] (0.001 mol % Rh relative to benzene) to 150° C. under 25 psig of propylene with Cu(OPiv)$_2$ (240 eq. relative to Rh) over 2 hours affords propenylbenzene products with a linear: branched (L:B) ratio of ~9:1. The total TO of alkenyl benzene products was 64, corresponding to ~53% yield relative to Cu(OPiv)$_2$.

Example 6.13

Heating a 10 mL benzene solution of rhodium(III) acetate [hexakis(acetato)triaquo-μ-oxotrirhodium(III) acetate] (0.001 mol % Rh relative to benzene) to 150° C. under air (1 atm) and 60 psig of ethylene with Cu(OPiv)$_2$ (240 eq. relative to Rh) and 480 eq. HOPiv over 36 hours generates 500 TO styrene and 45 TO stilbene.

Example 6.14

With 0.001 mol % Rh (Rh source=rhodium(III) acetate, hexakis(acetato)triaquo-μ-oxotrirhodium(III) acetate) relative to 10 mL benzene, under 35 psig of propylene with Cu(OAc)$_2$ (240 eq. relative to Rh) and 480 equiv. HOPiv at 150° C. for 42 h, an ~8:1 ratio of linear vs branched products and 977 TO of alkenyl products were obtained.

Example 6.15

Heating a 10 mL benzene/acetic acid solution [50/50 (v/v) benzene/acetic acid] of rhodium(III) acetate [hexakis(acetato)triaquo-μ-oxotrirhodium(III) acetate] (0.001 mol % Rh relative to benzene) to 150° C. under air and 60 psig of ethylene over 48 hours affords 277 TO of styrene and 6 TO of stilbene.

Example 6.16

A 10 mL benzene/acetic acid solution [50/50 (v/v) benzene/acetic acid] of rhodium(III) acetate [hexakis(acetato) triaquo-μ-oxotrirhodium(III) acetate] (0.001 mol % Rh relative to benzene) was charged with air and 35 psig of propylene and heated to 150° C. for 48 hours to afford ~165 TO of propenylbenzene products with a linear:branched products (L:B) ratio of ~3:1.

Example 7. Examples of Acid Addition

Example 7.1

The loading of Rh(μ-TFA)(5-FP) is 0.001 mol % (relative to benzene) and 240 eq. Cu(II) salts (relative to Rh, Cu(OPiv)₂ or Cu(OAc)₂) are added as the in situ oxidant. Additionally, 480 eq. HOPiv (relative to Rh) are added to help with recycling the Cu oxidant. Propylene (30 psig) is the olefin source. After all Cu salts are consumed, the reactor is purged with 1 atm of air and the Cu oxidant will be regenerated at 120° C. with 50 psig of N₂ over-pressure. The reaction can achieve over 1500 TOs (over 1000% yield relative to Cu oxidant) with multiple Cu recycling procedures. The linear to branched product ratio is maintained at about 10:1.

Example 7.2

In this reaction, the loading of Rh(μ-TFA)(5-FP) is 0.0001 mol % (relative to benzene) and 2400 eq. (relative to Rh) Cu(II) salts (Cu(OPiv)₂ or Cu(OAc)₂) are added as in situ oxidant. HOPiv (48000 eq., relative to Rh) is added to help recycle the Cu oxidant. Air is present in situ and propylene (30 psig) is the olefin source. In this reaction, the Cu oxidant is consumed and subsequently re-oxidized in situ by O₂ and HOPiv. By this method, over 10,000 TOs have been achieved without catalyst deactivation. The linear to branched product ratio is about 8:1.

Example 8. Reactions of Mono-Substituted Arenes Other than Toluene

Example 8.1

A solution containing [Rh(μ-OAc)(η²-C₂H₄)₂]₂ (0.005 g, 0.012 mmol, 0.001 mol % of rhodium relative to benzene), hexamethylbenzene (0.075 g, 0.45 mmol), and chlorobenzene (200 mL) was prepared in a volumetric flask. Fisher-Porter reactors were charged with 10 mL of the Rh stock solution and Cu(OAc)₂ (0.050 g, 0.28 mmol). The vessels were sealed, pressurized with propylene (25 psig), and subsequently stirred and heated to 150° C. Analsysis of products revealed alkenylation with a ratio of ortho:meta: para 1:11:7 and a linear:branched ratio of 10:1.

Example 8.2

A solution containing [Rh(μ-OAc)(η²-C₂H₄)₂]₂ (0.005 g, 0.012 mmol, 0.001 mol % of rhodium relative to benzene), hexamethylbenzene (0.075 g, 0.45 mmol), and anisole (200 mL) was prepared in a volumetric flask. Fisher-Porter reactors were charged with 10 mL of the Rh stock solution and Cu(OAc)₂ (0.050 g, 0.28 mmol). The vessels were sealed, pressurized with propylene (25 psig), and subsequently stirred and heated to 150° C. Analsysis of products revealed alkenylation with a ratio of ortho:meta:para 1:2.4:6.4 and a linear:branched ratio of 8:1.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The present disclosure will be better understood upon review of the following features, which should not be confused with the claims.

Feature 1. A method of making alkenyl arenes, the method comprising contacting an arene and an olefin in the presence of an effective amount of a rhodium catalyst and an oxidant at an elevated temperature for a period of time to produce the alkenyl arenes.

Feature 2. The method according to Feature 1, wherein the method is performed in the presence of halogens.

Feature 3. The method according to Feature 1, wherein the method is performed in a halogen-free environment.

Feature 4. The method according to any one of Features 1-3, wherein the rhodium catalyst has a structure according to the following formula

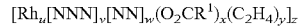

where [NNN] is a tridentate nitrogen donor ligand, [NN] is a bidentate nitrogen donor ligand, and $R^1$ is a substituted or unsubstituted $C_1$-$C_{12}$ alkyl or heteroalkyl; where u, v, w, x, y, and z are integers such that u is 1 or 2; v and w are 0 or 1 so long as v+w is less than or equal to 1; x is an integer from 0 to 4; y is an integer from 0 to 2; and z is 1 or 2.

Feature 5. The method according to any one of Features 1-4, wherein, wherein v+w is 1; and wherein z is 1.

Feature 6. The method according to any one of Features 1-4, wherein v is 1; and wherein then x+y is 1.

Feature 7. The method according to any one of Features 1-4, wherein w is 1; and wherein x+y is 2.

Feature 8. The method according to any one of Features 2-7, wherein $R^1$ is $CH_3$ or $CF_3$.

Feature 9. The method according to any one of Features 2-8, wherein [NNN] is an NNN pincer ligand having a structure according to the formula

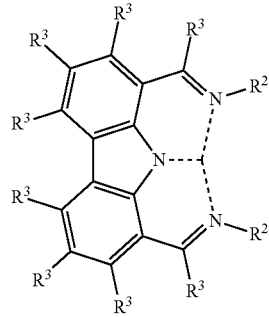

where each occurrence of $R^2$ is independently a hydrogen or a substituted or unsubstituted $C_1$-$C_3$ alkyl or heteroalkyl; and wherein each occurrence of $R^3$ is independently a hydrogen, a halogen, a hydroxyl, or a substituted or unsubstituted $C_1$-$C_3$ alkyl or heteroalkyl.

Feature 10. The method according to any one of Features 2-9, wherein [[NN] bidentate nitrogen donor ligand having a structure according to either of the following formulas

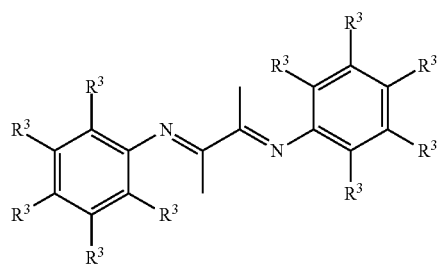

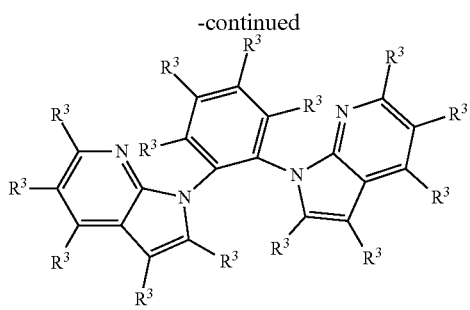

where each occurrence of R³ is independently a hydrogen, a halogen, a hydroxyl, or a substituted or unsubstituted C₁-C₃ alkyl or heteroalkyl.

Feature 11. The method according to any one of Features 1-10, wherein the catalyst is a heterogeneous Rh catalyst such as Rh on metal oxide.

Feature 12. The method according to Features 11, wherein a loading of the rhodium catalyst is about 0.00001 mol % to about 0.1 mol % relative to the arene.

Feature 13. The method according to any one of Features 1-12, wherein a loading of the oxidant is about 50 equivalents to about 5,0000 equivalents relative to the loading of the rhodium catalyst.

Feature 14. The method according to any one of Features 1-13, wherein the oxidant is a Cu(II) salt.

Feature 15. The method according to any one of Features 1-14, wherein the oxidant is air or purified oxygen.

Feature 16. The method according to any one of Features 1-15, wherein the first elevated temperature is about 150° C. to about 180° C.

Feature 17. The method according to any one of Features 1-16, wherein the first period of time is about 12 hours to about 120 hours.

Feature 18. The method according to any one of any one of Features 1-17, wherein a linear to branched ratio (L:B ratio) of the alkenyl arenes is about 2:1 to about 99:1.

Feature 19. The method according to any one of any one of Features 1-18, wherein the arene is a mono-substituted benzene; and wherein the alkenyl arenes comprise one or both of a meta-substituted alkenyl arene and a para-substituted alkenyl arene.

Feature 20. The method according to any one of Features 1-19, wherein a total amount of the meta-substituted alkenyl arene and the para-substituted alkenyl arene is about 85 mol % to about 100 mol % based upon a total amount of the alkenyl arene.

Feature 21. The method according to any one of Features 1-20, wherein the mono-substituted benzene comprises one or more of toluene, chlorobenzene, and anisole.

Feature 22. The method according to any one of Features 1-21, wherein the olefin comprises one or more of propylene, 1-pentene, neohexene, and isobutylene.

Feature 23. The method according to any one of Features 1-22, wherein the olefin comprises a linear or branched, substituted or unsubstituted alpha olefin having from 3 to about 30 carbon atoms.

Feature 24. The method according to any one of Features 1-23, wherein the arene comprises a polyaromatic.

Feature 25. The method according to any one of Features 1-24, wherein the polyaromatic is selected from the group consisting of substituted and unsubstituted naphthalene, anthracene, tetracene, and other polyaromatic compounds having from 2 to 5 fused aromatic rings.

Feature 26. The method according to any one of Features 1-25, the method further comprising dehydrogenation of the alkenyl arenes to form alkyl arenes.

Feature 27. The method according to any one of Features 1-26, wherein the dehydrogenation comprises contacting the alkenyl arenes and hydrogen in the presence of a hydrogenation catalyst at a second elevated temperature for a second period of time to produce the alkyl arenes.

Feature 28. The method according to any one of Features 1-27, wherein the second elevated temperature is about 100° C. to about 300° C.

Feature 29. The method according to any one of Features 1-18, wherein the dehydrogenation comprises combining the alkenyl arenes and the ethanol at an elevated pressure of about 100 psig to about 5000 psig.

Feature 30. The method according to any one of Features 1-29, wherein the second period of time is about 1 hour to about 72 hours.

Feature 31. The method according to any one of Features 1-30, wherein a linear to branched ratio (L:B ratio) of the alkyl arenes is about 2:1 to about 99:1.

Feature 32. The method according to any one of Features 1-31, wherein the arene is benzene; wherein the olefin is ethylene; and wherein the alkenyl arene is styrene.

Feature 33. The method according to Feature 32, wherein the styrene is produced with over 95% yield and a ratio of styrene to trans-stilbene of at least 98:1.

Feature 34. The method according to any one of Features 1-33 further comprising that the arene and olefin are contacted in the presence of the rhodium catalyst and an effective amount of an acid to improve one or both of a longevity of the rhodium catalyst and a linear to branched ratio (L:B ratio) of the alkenyl arenes.

Feature 35. A method of making a 2,6-dimethylnapthalene (DMN) or 2,6-methylethylnapthalene (MEN), the method comprising: making a pentenyl or hexenyl toluene by a method according to any one of Features 1-34; and dehydroaromatization of the pentenyl or hexenyl toluene to form the DMN or MEN.

Feature 36. The method according to Feature 35, wherein the dehydroaromatization comprises contacting the pentenyl or hexenyl toluene with a combination of a dehydrogenation catalyst and a zeolite catalyst.

Feature 37 The method according to Feature 35 or Feature 36, wherein the dehydrogenation catalyst is an iridium complex with a pincer-type ligand.

We claim:

1. A method of making alkenyl arenes, the method comprising contacting an arene and an olefin in the presence of an effective amount of a rhodium catalyst and an oxidant at an elevated temperature for a period of time to produce the alkenyl arenes, wherein the rhodium catalyst is a heterogeneous Rh(II) or Rh(III) catalyst.

2. The method according to claim 1, wherein a linear to branched ratio (L:B ratio) of the alkenyl arenes is about 2:1 to about 99:1.

3. The method according to claim 1, wherein the arene is a mono-substituted benzene; and
wherein the alkenyl arenes comprise one or both of a meta-substituted alkenyl arene and a para-substituted alkenyl arene.

4. The method according to claim 3, wherein a total amount of the meta-substituted alkenyl arene and the para-substituted alkenyl arene is about 85 mol % to about 100 mol % based upon a total amount of the alkenyl arene.

5. The method according to claim 3, wherein the monosubstituted benzene comprises one or more of toluene, chlorobenzene, and anisole.

6. The method according to claim 3, wherein the olefin comprises one or more of propylene, 1-pentene, neohexene, and isobutylene.

7. The method according to claim 3, wherein the olefin comprises a linear or branched, substituted or unsubstituted alpha olefin having from 3 to about 30 carbon atoms.

8. The method according to claim 1, wherein the arene comprises a polyaromatic.

9. The method according to claim 8, wherein the polyaromatic is selected from the group consisting of substituted and unsubstituted naphthalene, anthracene, tetracene, and other polyaromatic compounds having from 2 to 5 fused aromatic rings.

10. The method according to claim 1, the method further comprising dehydrogenation of the alkenyl arenes to form alkyl arenes.

11. The method according to claim 10, wherein the hydrogenation comprises contacting the alkenyl arenes and hydrogen in the presence of a hydrogenation catalyst at a second elevated temperature for a second period of time to produce the alkyl arenes.

12. The method according to claim 11, wherein the second elevated temperature is about 100° C. to about 300° C.

13. The method according to claim 11, wherein the hydrogenation comprises combining the alkenyl arenes and the ethanol at an elevated pressure of about 100 psig to about 5000 psig.

14. The method according to claim 11, wherein the second period of time is about 1 hour to about 72 hours.

15. The method according to claim 1, wherein the arene is benzene;
wherein the olefin is ethylene; and
wherein the alkenyl arene is styrene.

16. The method according to claim 15, wherein the styrene is produced with over 95% yield and a ratio of styrene to trans-stilbene of at least 98:1.

17. The method according to claim 1, further comprising that the arene and olefin are contacted in the presence of the rhodium catalyst and an effective amount of an acid to improve one or both of a longevity of the rhodium catalyst and a linear to branched ratio (L:B ratio) of the alkenyl arenes.

18. A method of making a 2,6-dimethylnapthalene (DMN) or 2,6-methylethylnapthalene (MEN), the method comprising:
making a pentenyl or hexenyl toluene by a method according to claim 1; and
dehydroaromatization of the pentenyl or hexenyl toluene to form the DMN or MEN.

19. The method according to claim 18, wherein the dehydroaromatization comprises contacting the pentenyl or hexenyl toluene with a combination of a dehydrogenation catalyst and a zeolite catalyst.

20. The method according to claim 19, wherein the dehydrogenation catalyst is an iridium complex with a pincer-type ligand.

21. The method of claim 1, wherein the heterogeneous Rh(II) or Rh(III) catalyst is selected from Rh nanoparticles on $SiO_2$, Rh nanoparticles on $Al_2O_3$, or Rh nanoparticles on a zeolite.

* * * * *